(12) United States Patent
Wallbridge et al.

(10) Patent No.: US 10,845,351 B2
(45) Date of Patent: Nov. 24, 2020

(54) APPARATUS AND METHOD FOR PROCESSING SIGNALS OBTAINED FROM PLANTS

(71) Applicant: Vivent sárl, Crans-près-Cèligny (CH)

(72) Inventors: Nigel Christopher Wallbridge, Crans-près-Cèligny (CH); Carrol Annette Plummer, Crans-près-Cèligny (CH); Martin Timms, Northumberland (GB); Caleb Carroll, Cochrane (CA); Nicholas Barker, Durham (GB)

(73) Assignee: Vivent sárl, Crans-près-Cèligny (FR)

( * ) Notice: Subject to any disclaimer, the term of this patent is extended or adjusted under 35 U.S.C. 154(b) by 221 days.

(21) Appl. No.: 15/753,791

(22) PCT Filed: Aug. 22, 2016

(86) PCT No.: PCT/EP2016/069823
§ 371 (c)(1),
(2) Date: Feb. 20, 2018

(87) PCT Pub. No.: WO2017/032750
PCT Pub. Date: Mar. 2, 2017

(65) Prior Publication Data
US 2018/0267006 A1    Sep. 20, 2018

(30) Foreign Application Priority Data
Aug. 21, 2015    (GB) .................................. 1514945.3

(51) Int. Cl.
*A01G 7/00* (2006.01)
*G01N 33/00* (2006.01)
*G01N 27/22* (2006.01)

(52) U.S. Cl.
CPC ........... *G01N 33/0098* (2013.01); *A01G 7/00* (2013.01); *G01N 27/22* (2013.01)

(58) Field of Classification Search
CPC ........................ G01N 27/22; G01N 33/0098
See application file for complete search history.

(56) References Cited

U.S. PATENT DOCUMENTS 3,688,309 A    8/1972    Volberg
3,967,198 A *  6/1976    Gensler ................... A61B 5/04
                                                   324/72

(Continued)

FOREIGN PATENT DOCUMENTS

DE    3722516 A1    1/1988
DE    102006041127 B3 *    3/2008    ............... A01G 7/00

(Continued)

OTHER PUBLICATIONS

Borges, Elisabeth et al, "Assessment of Physio9logical States of Plants in situ An Innovative Approach to the Use of Electrical Impedance Spectroscopy", Mar. 24, 2018, Internet: URL:http://www.thinkmind.org/download.php?articleid=biotechno_2013_1_10_60080.

(Continued)

*Primary Examiner* — Jamel E Williams
(74) *Attorney, Agent, or Firm* — Wolter Van Dyke Davis, PLLC; Robert L. Wolter

(57) ABSTRACT

A method of processing signals comprising: obtaining an electrical signal from one or more plant specimens; and processing said obtained electrical signal to generate plant data; wherein the plant data is data indicative of a characteristic of said one or more plant specimens, wherein said characteristic comprises at least one of: a measure of the health of said one or more plant specimens, a measure of the vitality of said one or more plant specimens, and a reaction to environmental changes of said one or more plant specimens.

22 Claims, 14 Drawing Sheets

(56) References Cited

U.S. PATENT DOCUMENTS

| | | | | |
|---|---|---|---|---|
| 5,224,769 | A * | 7/1993 | Holbrook | G01N 27/223 |
| | | | | 324/664 |
| 5,819,467 | A * | 10/1998 | Zucker | A01G 7/04 |
| | | | | 47/1.3 |
| 6,202,479 | B1 * | 3/2001 | Frybarger | A01G 27/008 |
| | | | | 324/694 |
| 6,870,376 | B1 * | 3/2005 | Gensler | A01G 7/00 |
| | | | | 324/663 |
| 7,956,624 | B2 * | 6/2011 | Beaulieu | A01G 7/00 |
| | | | | 324/692 |
| 7,994,802 | B2 * | 8/2011 | Osypka | A01G 7/00 |
| | | | | 324/692 |
| 8,289,035 | B1 | 10/2012 | Gensler | |
| 9,075,698 | B2 * | 7/2015 | Stachon | A01G 7/00 |
| 9,719,952 | B1 * | 8/2017 | Gensler | G01N 33/188 |
| 9,756,796 | B2 * | 9/2017 | Gimenez Calbo | G01L 1/02 |
| 2009/0278555 | A1 * | 11/2009 | Osypka | A01G 7/00 |
| | | | | 324/692 |
| 2014/0109658 | A1 | 4/2014 | Kah, Jr. | |
| 2015/0015697 | A1 * | 1/2015 | Redden | G01N 33/0098 |
| | | | | 348/89 |

FOREIGN PATENT DOCUMENTS

| | | |
|---|---|---|
| DE | 102006041127 B3 | 3/2008 |
| EP | 1726924 A1 | 11/2006 |
| GB | 2193325 A | 2/1988 |
| WO | 2004071172 A1 | 8/2004 |
| WO | 2007128122 A1 | 11/2007 |
| WO | 2014017940 A1 | 1/2014 |

OTHER PUBLICATIONS

PCTEP2016/069823; International Search Report and Written Opinion, dated Oct. 27, 2016; 13 pages.

Borges, E. et al., "Early Detection and Monitoring of Plant Diseases by Bioelectric Impedance Spectroscopy", 4 pages.

GB1514945.3; UKIPO Examination Report; dated Feb. 8, 2018, 4 pages.

GB1514945.3; UKIPO Examination Report; dated Sep. 29, 2017; 5 pages.

GB1514945.3; UKIPO Examination Report; dated Jun. 19, 2016; 4 pages.

* cited by examiner

APPARATUS AND METHOD FOR PROCESSING SIGNALS OBTAINED FROM PLANTS

The present invention relates to a method and apparatus for processing signals obtained from plants. More particularly, but not exclusively, the present invention relates to a method and apparatus for processing signals so as to monitor the health or vitality of plant specimens and/or to make evident the plant specimens' state and reaction to changes in their environment.

It is well known that electric potential differences, or membrane potentials, are maintained across cell membranes in many biological organisms, such as plants. The potential differences are typically of the order of tens of millivolts, and in some cases are relatively stable over time. However, in some cases, the potential difference can vary with time. Such variation can, for example, be used to transmit signals between different parts of a cell, or even different cells within an organism. Such potential variations may be known as action potentials, and typically involve a relatively short-lasting event in which the potential differences across a cell membrane rises and falls, according to a known and repeatable trajectory.

Such action potentials, in plants at least, may be associated with events, such as, for example, the triggering and closing of a Venus flytrap.

Further, it has been observed that by capturing electrical signals generated by a plant during such an event, and re-playing the captured signals to the plant at a later time, it is possible to trigger a further occurrence of the same event. That is, a Venus flytrap which closes in response to a physical stimulation generates an action potential, which can be captured. By re-playing the captured action potential to the Venus flytrap it is possible to trigger it to close once more, in the absence of any physical stimulus.

However, action potentials in plants are generally only associated with physical or chemical events, and do not have any known relationship with the health or vitality of a plant specimen. Rather, they are part of the signalling within the plant required to bring about the occurrence of a physical event.

It is an object of the invention to provide a way of monitoring the health or vitality of plant specimens and to make evident any reaction of the plant to environmental changes.

According to a first aspect of the invention there is provided a method of processing signals comprising obtaining an electrical signal from one or more plant specimens, and processing said obtained electrical signal to generate plant data. The plant data is data indicative of a characteristic of said one or more plant specimens, wherein said characteristic comprises at least one of: a measure of the health of said one or more plant specimens, a measure of the vitality of said one or more plant specimens, and a reaction to environmental changes of said one or more plant specimens.

By obtaining electrical signals from plants and processing the obtained electrical signal it is possible to generate plant data related to the health, vitality or environment of the plants. While it is known that some signals obtained from may indicate activity, such as action potential events, it will be appreciated that whereas an action potential event may indicate a specific response to a physical stimulus, by obtaining and processing electrical signals it is possible to understand and control aspects of health and vitality of a plant and to understand and control an environment of a plant.

Said processing may comprise identifying one or more components of said obtained electrical signal which has a predetermined characteristic indicative of said characteristic.

Said processing may comprise: comparing said obtained electrical signal with one or more reference signals; and identifying one or more components of said obtained electrical signal which has a predetermined relationship with said one or more reference signals.

The obtained electrical signal and/or the one or more reference signals may be frequency domain signals or a time domain signals.

Comparing said obtained electrical signal with one or more reference signals may comprise generating data indicative of a relationship between said obtained electrical signal and said one or more reference signals.

Identifying one or more components of said obtained electrical signal which has a predetermined relationship with said one or more reference signals may comprise determining whether said generated data satisfies a predetermined criterion.

The method may further comprise generating match data comprising data indicating which of a plurality of reference signals have a predetermined relationship with said obtained electrical signal, wherein the generated match data is said plant data.

The method may further comprise generating said one or more reference signals based upon a plurality of reference electrical signals obtained from one or more plant specimens while said one or more plant specimens are exposed to a predetermined condition.

Said predetermined condition may comprise at least one of: a thermal condition of said one or more plant specimens, a hydration condition of said one or more plant specimens, a nutrition condition of said one or more plant specimens, an illumination condition of said one or more plant specimens, a mechanical condition of said one or more plant specimens, an atmospheric condition of said one or more plant specimens, a threat associated with said one or more plant specimens, and a chemical condition of said one or more plant specimens.

Generating said one or more reference signals may comprise calculating an average of the plurality of reference electrical signals.

Obtaining the electrical signal may comprise sensing an electrical signal emitted by said one or more plant specimens.

The method may further comprise converting said sensed electrical signal to a digital signal.

The method may comprise converting said sensed electrical signal to a digital signal having at least 14-bit amplitude resolution. Preferably the method comprises converting said sensed electrical signal to a digital signal with at least 16-bit amplitude resolution, more preferably with at least with at least 24-bit amplitude resolution, and even more preferably with at least with at least 32-bit amplitude resolution.

The method may further comprise performing signal conditioning on said obtained electrical signal.

Said signal conditioning may comprise performing analogue and/or digital signal conditioning. Said signal conditioning may comprise filtering said obtained electrical signal.

Obtaining the electrical signal may comprise sensing at least one electrical signal emitted by said one or more plant specimens.

Obtaining the electrical signal may comprise monitoring a potential difference between a reference electrode associated with a reference potential and a capture electrode associated with said one or more plant specimens.

The method may further comprise providing said reference electrode in contact with a growth medium in contact with said one or more plant specimens.

The method may further comprise providing said capture electrode in contact with said one or more plant specimens.

The method may further comprise electromagnetically shielding an electrical signal obtained by said reference electrode and/or said capture electrode.

Obtaining the electrical signal may comprise electromagnetically shielding said one or more plant specimens during the obtaining of the electrical signal.

The obtained electrical signal may comprise at least one signal component having a frequency of at least 10 Hz.

Said at least one signal component having a frequency of at least 10 Hz may comprise said identified one or more components.

Said obtained electrical signal may comprise at least one signal component having a frequency of at least 1 kHz.

By obtaining electrical signals from plants which comprise at least one signal component having a frequency of at least 1 kHz and processing the obtained electrical signal it is possible to generate plant data related to the health, vitality or environment of the plants. While some low frequency signals may indicate activity such as action potential events, it will be appreciated that in order to capture electrical signals which are indicative of particular plant health or vitality characteristics, or responses to an environmental condition, signals having components of at least 1 kHz should be captured.

Said obtained electrical signal may comprise at least one signal component having a frequency of at least 10 kHz. Said obtained electrical signal may comprise at least one signal component having a frequency of at least 20 kHz.

Said obtained electrical signal may comprise at least one signal component having a frequency of up to 125 kHz.

The method may comprise generating a plant control signal based upon the plant data.

This method allows plant growth, health, vitality to be monitored, and for the monitored data (i.e. plant data) to be used as an input to a control system, for example to control some aspect of the environment in which the plant is located, so as to influence the plant growth, health or vitality.

The plant control signal may be arranged to affect said one or more plant specimens.

The method may further comprise controlling an environment of the one or more plant specimens based upon the plant data.

The environment of the one or more plant specimens may be an environment in which at least one of the one or more plant specimens is located The plant control signal may be arranged to control at least one parameter of the environment of the one or more plant specimens.

The plant control signal may be arranged to adjust at least one parameter of the environment of the one or more plant specimens.

Controlling an environment of the one or more plant specimens may comprise controlling the illumination of said one or more plant specimens. Controlling an environment of the one or more plant specimens may comprise controlling the irrigation of said one or more plant specimens. Controlling an environment of the one or more plant specimens may comprise controlling the insecticide application to said one or more plant specimens. Controlling an environment of the one or more plant specimens may comprise controlling the fungicide application to said one or more plant specimens. Controlling an environment of the one or more plant specimens may comprise controlling the temperature of said one or more plant specimens. Controlling an environment of the one or more plant specimens may comprise controlling the humidity of said one or more plant specimens. Controlling an environment of the one or more plant specimens may comprise controlling the nutrition of said one or more plant specimens. Various aspects of the environment of the one or more plant specimens such as, for example, those referred to above, may be controlled alone or in combination.

Generating the plant control signal based upon the plant data may comprise determining whether the plant data meets a predetermined criterion.

Controlling an environment of said one or more plant specimens may comprise determining whether said plant data meets a predetermined criterion.

Determining whether said plant data meets said predetermined criterion may be based upon plant data relating to a plurality of plant specimens.

Determining whether said plant data meets said predetermined criterion may comprise determining whether plant data relating to a predetermined number of plant specimens meets a predetermined criterion.

Generating the plant control signal based upon the plant data may comprise: determining whether the plant data meets a predetermined criterion; and generating the plant control signal if the plant data meets a predetermined criterion.

The method may further comprise generating an output signal based upon the plant data.

The output signal may be an audible signal or a visible signal.

The output signal may be modulated so as to have at least one characteristic which is dependent upon said plant data.

The method may further comprise communicating said plant data from a first processing device to second processing device.

Said first processing device may be arranged to sense an electrical signal emitted by said one or more plant specimens.

Said second processing device may be a mobile computing device.

The method may further comprise storing said plant data in a storage device.

Obtaining said electrical signal from one or more plant specimens may comprise retrieving said electrical signal from a storage device.

Said processing may comprise transforming said obtained electrical signal from a time domain signal to a frequency domain signal, said frequency domain signal comprising a plurality of frequency components each having a respective amplitude value.

Said processing may further comprise selecting a plurality of frequency components contained within said frequency domain signal which satisfy a predetermined criterion.

Said processing may comprise selecting a plurality of frequency components contained within said frequency domain signal based upon said amplitude values.

Said processing may comprise selecting a plurality of frequency components contained within said frequency domain signal wherein each of the selected plurality of frequency components has an amplitude value which is greater in magnitude than each of the amplitude values associated with the un-selected frequency components.

Said selecting said plurality of frequency components may comprise: sorting said frequency components based upon the magnitude of each of the amplitude values associated with the frequency components; and selecting said plurality of frequency components from the sorted frequency components.

The method may further comprise generating a reference frequency domain signal, said reference frequency domain signal comprising a plurality of frequency components each having a respective amplitude value, each amplitude value being based upon a plurality of amplitude values associated with a corresponding frequency component of a respective plurality of frequency domain signals.

The method may comprise selecting a plurality of frequency components contained within said reference frequency domain signal wherein each of the selected frequency components has an amplitude value which is greater in magnitude than each of the amplitude values associated with the un-selected frequency components; and selecting a plurality of frequency components contained within said frequency domain signal wherein each of the selected frequency components has a corresponding selected frequency component within said reference frequency domain signal.

The method may further comprise generating a normalised frequency domain signal by normalising the amplitude of said amplitude values.

Normalising the amplitude of said amplitude components may comprise: subtracting a respective mean amplitude value corresponding to the respective frequency component from each of the amplitude values.

Normalising the amplitude of said amplitude components may further comprise: dividing each of the remaining amplitude values by a standard deviation amplitude value corresponding to the respective frequency component.

The mean amplitude value and/or standard deviation amplitude value may be generated based upon a reference frequency domain signal.

The method may further comprise processing said normalised frequency domain signal to identify a change in said characteristic of said one or more plant specimens.

Said plant data may comprise data indicative of at least one of: a thermal condition of said one or more plant specimens, a hydration condition of said one or more plant specimens, a nutrition condition of said one or more plant specimens, an illumination condition of said one or more plant specimens, a mechanical condition of said one or more plant specimens, an atmospheric condition of said one or more plant specimens, a threat associated with said one or more plant specimens, and a chemical condition of said one or more plant specimens.

According to a second aspect of the invention there is provided an apparatus for processing signals arranged to perform a method according to the first aspect of the invention.

According to a third aspect of the invention there is provided an apparatus for processing signals, the apparatus comprising: a capture device configured to generate a signal based upon an electrical signal received from one or more plant specimens; a processor arranged to process said obtained electrical signal to generate plant data wherein the plant data is data indicative of characteristic of said one or more plant specimens, wherein said characteristic comprises at least one of; a measure of the health of said one or more plant specimen, the vitality of said one or more plant specimen, or a reaction to environmental changes of said one or more plant specimens.

The apparatus may further comprise at least one electrode configured to receive an electrical signal from one or more plant specimens.

The apparatus may further comprise shielding configured to reduce the effect of electromagnetic radiation upon said generated signal.

The apparatus may further comprise an analogue to digital converter arranged to convert the electrical signal received from one or more plant specimens to a digital signal.

It will be appreciated that features discussed in the context of one aspect of the invention can be applied to other aspects of the invention. In particular, where features are described as being carried out by the method in the first aspect of the invention it will be appreciated that such features can be used in combination with an apparatus according to the second or third aspects of the invention.

The methods of the first aspect of the invention can be carried out in any convenient way. In particular, the method may be carried out by an apparatus and such an apparatus is therefore provided by the invention. The apparatus may be provided by any appropriate hardware elements or collections of hardware elements. For example the apparatus may comprise a microcontroller which reads and executes instructions stored in a memory, the instructions causing the apparatus to carry out a method as described herein. Alternatively the apparatus may comprise an ASIC or FPGA. Further the invention also provides computer programs which can be executed by a processor of an apparatus so as to cause the apparatus to be controlled in the manner described above. Such computer programs can be stored on computer readable media such as non-tangible, not transitory computer readable media.

Embodiments of the invention will now be described with reference to the accompanying drawings in which.

Figure 1:
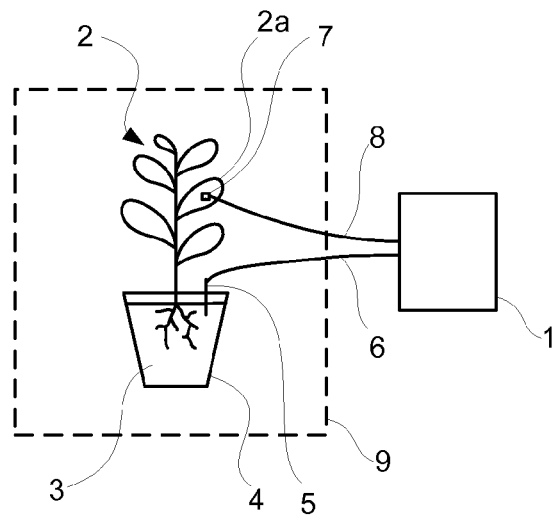
FIG. 1 illustrates a plant health monitoring device according to embodiments of the invention.

As shown in FIG. 1, a plant health monitoring device 1 is arranged to monitor the health of a plant 2. The plant 2 is grown in a growth medium 3 and contained within a plant pot 4. The growth medium 3 may be any suitable medium in which the plant 2 is able to grow. For example, the medium 3 may be soil, compost, water or the like. A reference electrode 5 is inserted into the medium 3 and connected, by a lead 6, to the plant health monitoring device 1. A capture electrode 7 is attached to a leaf 2a of the plant 2, and is also connected, by a second lead 8, to the plant health monitoring device 1. It will be appreciated that the capture electrode 7 (or a plurality of capture electrodes) may be attached to a plurality of leaves of the plant 2. Alternatively, the capture electrode 7 may be attached to other plant structures, such as, for example, a stem, or portion of root of the plant 2. Similarly, the reference electrode 5 may comprise a plurality of reference electrodes.

An electromagnetic shield 9 is provided so as to shield the plant 2 from external sources of electromagnetic radiation. The electromagnetic shield 9 may, for example, comprise a Faraday cage which effectively surrounds the plant 2 during monitoring.

Figure 2:
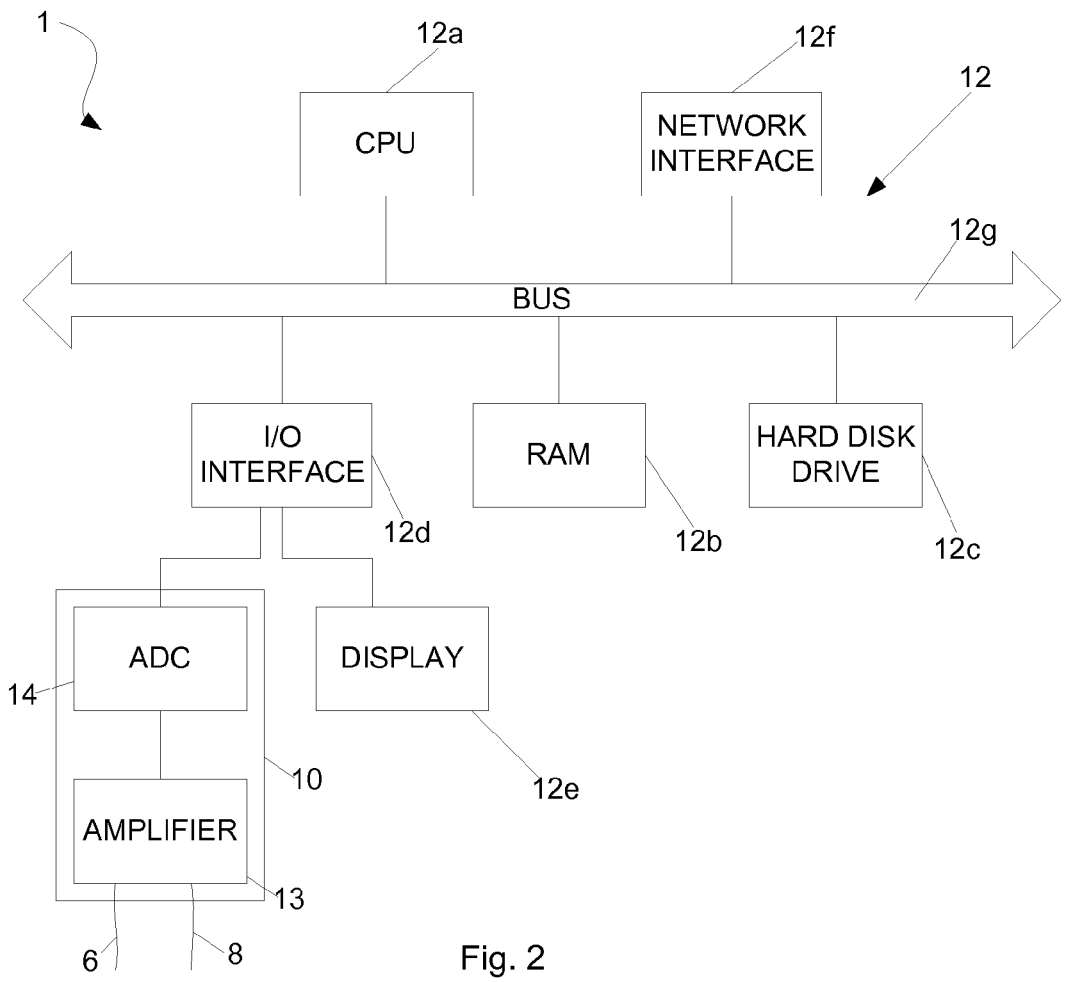
FIG. 2 illustrates the device shown in FIG. 1 in more detail.

As shown in more detail in FIG. 2, the plant health monitoring device 1 comprises a data acquisition module 10 and a controller 12. The leads 6, 8 are each connected to the data acquisition module 10. The data acquisition module 10 comprises an amplifier 13, such as, for example, a high input impedance differential amplifier, and an analog-to-digital converter (ADC) 14. The data acquisition module 10 may further comprise any additional components which allow for the acquired data to be processed as described in more detail below. For example, the data acquisition module 10 may comprise various analogue and/or digital filtering devices arranged to perform signal conditioning on the acquired data.

The controller 12 comprises a CPU 12a which is configured to read and execute instructions stored in a volatile memory 12b which takes the form of a random access memory. The volatile memory 12b stores instructions for execution by the CPU 12a and data used by those instructions. For example, in use, the data acquired by the data acquisition module 10 may be stored in the volatile memory 12b.

The controller 12 further comprises non-volatile storage in the form of a hard disc drive 12c. The data acquired by the data acquisition module 10 may be stored on the hard disc drive 12c. The controller 12 further comprises an I/O interface 12d to which are connected data capture and peripheral devices used in connection with the controller 12 a display 12e is configured so as to display output from the controller 12. The display 12e may, for example, display a representation of the data acquired by the data acquisition module 10. The display 12e may be provided locally to the plant health monitoring device 1 (e.g. as a screen), or remotely from the plant health monitoring device 1. For example, a display associated with a separate device (e.g. a mobile computing device) may be used as a display for the plant health monitoring device 1.

Additionally, the display 12e may display images generated by processing of the data acquired by the data acquisition module 10. Additionally, a touchscreen associated with the display 12e may operate as a user input device, so as to allow a user to interact with the controller 12. Alternatively or additionally, separate input devices may be also connected to the I/O interface 12d. A network interface 12f allows the controller 12 to be connected to an appropriate computer network so as to receive and transmit data from and to other computing devices. The CPU 12a, volatile memory 12b, hard disc drive 12c, I/O interface 12d, and network interface 12f, are connected together by a bus 12g.

In addition to the peripheral devices described above being connected to the I/O interface 12d, the data acquisition module 10 is also connected to the I/O interface 12d. In more detail, an input of the data acquisition module 10 is connected to the electrodes 5, 7 via the leads 6, 8. The output of the data acquisition module 10 is in turn connected to the I/O interface 12d. By virtue of these connections, potential differences sensed at the electrodes 5, 7 can be conditioned (e.g. amplified) and converted to a digital signal by the data acquisition module 10 and subsequently processed by the CPU 12a. Such processing is described in more detail below.

Figure 3:
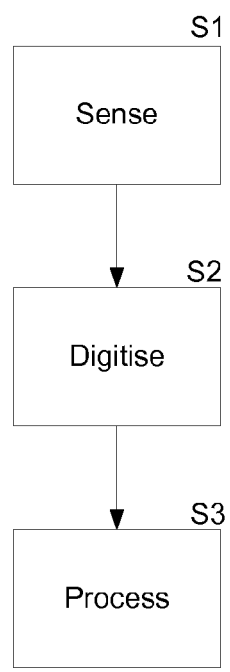
FIG. 3 shows steps of a process carried out by the device of FIG. 1.

As illustrated by FIG. 3, the plant health monitoring device 1 performs a series of actions to monitor the health of the plant 2, and to make evident any reaction of the plant to environmental changes. As a first step, S1, the plant health monitoring device 1 senses an electrical signal generated by the plant 2. This sensing process involves the electrical signal passing from the capture electrode 7 to the lead 8, and on to the data acquisition module 10. Simultaneously the reference electrode 5 provides, via the lead 6, the data acquisition module 10 with a measure of the voltage of the growth medium 3, and hence the voltage of the environment in which the plant 2 is growing. The amplifier 13 within the data acquisition module 10 monitors the differential voltage established between the first and second leads 6, 8, and thus the difference in potential between the reference and capture electrodes 5, 7. In this way, the amplifier 13 is able to monitor the local potential fluctuations at the surface of the leaf 2a, relative to the growth medium 3. The potential of the growth medium 3 is considered to represent the average potential of the base of the plant 2 as a whole, while individual leaves of the plant 2 are known to exhibit local potentials which vary in time relative to the average potential. Moreover, the presence of the reference electrode 5 allows the effect of any local fluctuations in earth level to be negated. Further, the reference electrode 5 may be maintained at a stable reference potential, such as, for example, zero volts, so as to pin the local earth level to the reference potential. It will be appreciated that an alternative reference potential may be used in some embodiments.

Once the differential voltage has been monitored by the amplifier 13, at step S2, an amplified electrical signal is converted by the ADC 14 to a digital signal. The ADC 14 may take any suitable form, and may be selected so as to provide a high degree of amplitude resolution. The ADC 14 may, for example, convert the analogue signal to a digital signal with a resolution of 24 bits (i.e. $2^{24}$ or 16777216 distinct levels). For a signal converted at the above resolution (i.e. 24 bits) having a maximum amplitude range of 10 V (i.e. ±5 V), each distinct level is equivalent to 0.0006 mV.

The digitised signal is passed to the CPU 12a (via the I/O interface 12d and bus 12g), where, at step S3, further processing is carried out as described in more detail below with reference to FIG. 4. The processing carried out by the CPU 12a allows electrical signals which are emitted by the plant 2 to be captured and identified. Such identification allows a user of the device 1 to gain a better understanding of various aspects of the health, vitality or reaction to environmental changes of the plant 2. For example, the processing carried out by the CPU 12a at step S3 on the digitised signal may be arranged to generate data indicative of a measure of the health or vitality of the plant 2.

In more detail, it has been realised that plants may emit signals which are related to their state. For example, while it has long been known that action potentials are used by plants as a mechanism for signalling, or actuating a physical or chemical response (e.g. a Venus fly trap closing), in addition to action potential signals, signals with smaller amplitudes and higher frequencies are also generated by a plant. By sensing, capturing, and analysing these signals it is possible to understand aspects of plant health and vitality which may be difficult to observe by other means (such as, for example, by observing visible characteristics alone). Further, by sensing, capturing, and analysing these signals it is also possible to automate aspects of plant care in a way which is responsive to plant needs, rather than being simply controlled by a predetermined schedule.

Captured electrical signals generally contain many different signal components, some of which may be evidence of action potentials (e.g. as exhibited by a 'sensitive' plant, such as, for example a Venus Flytrap—some examples of which are described in more detail below) and which may have a signal amplitude of the order of tens of mV. However, in contrast to such large signal waveforms the captured electrical signals may also contain small perturbations. Such small perturbations may not be immediately apparent when signals are examined at a temporal or amplitude resolution which is selected so as to be optimal for larger action potential events. However, when examined in more detail, it has been realised that these smaller perturbations are evidence of transient electrical signals or signal components which are also present, rather than being a result of noise or measurement artefacts. That is, in addition to the significant (i.e. tens of mV) potential fluctuations observed during an action potential event, these smaller perturbations are transient electrical signals or signal components which can be considered to be indicative of a state of a plant's health or vitality or evidence of the plant's response to its environment.

Such transient electrical signals or signal components, when examined in more detail, may, for example, generally correspond to one of a number of characteristic waveforms. For example, a transient electrical signal may be an occurrence of a transient electrical signal having a predetermined and repeatable characteristic waveform. Such transient electrical signals may, for example, have durations of the order of milliseconds or seconds, and amplitudes of the order of millivolts. Alternatively, a signal component may have a particular characteristic frequency spectrum.

Transient electrical signals can be identified as corresponding to a characteristic waveform and/or classified by comparison with reference waveforms. For example, portions of a captured electrical signal can be compared to reference waveforms so as to identify the occurrence of particular ones of known characteristic waveforms or transient electrical signals which are represented by those reference waveforms. Further such reference waveforms may be known to correspond to a particular plant health or vitality characteristic. It will also be appreciated that the reference waveforms may be indicative of, or modelled upon, a particular occurrences of an observed transient electrical signals in a plant specimen such that a captured transient electrical signal may not correspond exactly to the reference signals in amplitude, duration, or waveform shape. However, by performing signal processing and analysis, it is possible to identify captured transient electrical signals which correspond to a reference waveform to an extent which is considered to be sufficient to classify the captured transient electrical signals as one of a known class of waveform.

Further, in addition to the direct comparison with reference waveforms, data relating to the frequency of occurrence of transient electrical signals, or to the intensity of occurrence may also be collected and analysed.

It will be appreciated that comparisons with reference waveforms (i.e. comparisons in shape and amplitude) are an example of one form of pattern identification, More generally, captured electrical signals are analysed in combination with reference signals or reference data so as to identify a similarity in some relevant aspect. Such a comparison may be performed in the frequency or time domain, or combination thereof.

Waveforms may, for example, be identified by being correlated against one or more reference waveforms or a template based upon previously collected waveforms. Various reference waveforms can be identified through experimental research during which plants are exposed to various conditions or stresses which are known to have an effect (e.g. an adverse effect) on a plant's health. Such conditions may, for example, be related to the hydration condition of a plant, the thermal condition of a plant, the illumination condition of a plant, the nutrition condition of a plant, the mechanical condition of a plant, the atmospheric condition of a plant, and/or a threat to the plant.

A hydration condition of a plant relates to the level of irrigation of that plant. A hydration condition of a plant, may, for example, be that a plant is adequately hydrated. Stresses related to the hydration condition of a plant may, for example, include allowing the growth medium in which the plant is growing to become completely dry, or continual oversaturation of the growth medium.

A thermal condition of a plant relates to the thermal history of that plant, that is, the temperature of the environment in which the plant is growing over a period of time. A thermal condition of the plant, may, for example, be that the plant is at an optimal temperature for growth. Stresses related to the thermal condition of a plant may, for example, include exposure to heat above a predetermined temperature (e.g. 60° C.) or exposure to cold below a predetermined temperature (e.g. 0° C.) although some plants have a much narrower temperature range.

An illumination condition of a plant relates to the intensity and quality of illumination of that plant over a period of time. An illumination condition of the plant, may, for example, be that the plant is receiving optimal illumination for growth (e.g. to perform photosynthesis). Stresses related to the illumination condition of a plant may, for example, include exposure to intense light above a predetermined level (e.g. illumination above a level which corresponds to direct sunlight, such as, for example 1700 micromoles per square metre per second photosynthetic photon flux density), exposure to filtered light at various intensities where only specific wavelengths of light can pass through the filter, exposure to various intensities of UV or Infrared light and/or continual darkness (such that the plant cannot perform photosynthesis).

Conditions related to the chemical condition of a plant may, for example, include, the chemical composition of the growth medium, including the concentration of particular salts within the growth medium, or the concentration of nitrogen within the growth medium.

Conditions related to the nutrition condition of a plant may, for example, relate to the presence of a particular nutrient (e.g. a chemical). Stresses related to a nutrition condition of a plant may, for example, include the plant lacking a particular nutrient.

Stresses related to the mechanical condition of a plant may include mechanical damage caused to the plant.

Conditions related to the atmospheric condition of a plant may, for example, include the concentration of gases within the atmosphere in which the plant is growing, such as, for example carbon dioxide. Stresses related to the atmospheric condition of a plant may, for example, include the presence of a pollutant in the local atmosphere, such as, for example, hydrogen sulphide or dust. Further, conditions related to the atmospheric condition of a plant may, for example, include the humidity of the environment in which the plant is growing or the atmospheric pressure in which the plant is growing.

Stresses related to a threat to a plant may include the presence of organisms (e.g. an insect or other pest, or a fungus) which may damage the plant.

In addition to externally influenced conditions or stresses, plants may exhibit different modes (which may be indirectly linked to external conditions), such as a growth mode, or a defence mode.

Electrical signals can be captured from plants when exposed to various ones of the above conditions (or others), with such captured signals being used to populate a library of reference waveforms. It will be appreciated that the references waveforms may be based upon such captured signals and may, for example be generated by performing suitable processing on such captured signals. Suitable processing may, for example, include filtering and/or averaging to reduce the effect of measurement artefacts or natural variation between signals. Similarly, processing may identify frequency spectra which are considered to be indicative of particular conditions or threats. Such identified frequency spectra can be used to generate reference spectra. Reference waveforms and reference spectra are example of reference data.

In subsequent use, electrical signals captured from plant specimens can be compared with reference data. Such a comparison can be performed with signal data received from a plant specimen in one (or more) of the time-domain, the frequency domain, and the wavelet domain.

It will be appreciated that in order to capture electrical signals which are indicative of particular plant health or vitality characteristics, signals with a variety of frequency components should be captured. Moreover, while some low frequency signals may indicate activity such as an action potential event, it will be appreciated that in order to capture electrical signals which are indicative of particular plant health or vitality characteristics, or responses to an environmental condition, signals having at least a predetermined minimum frequency component should be captured. For example, in some embodiments, a predetermined minimum frequency component of at least 10 Hz allows electrical signals which are indicative of particular plant health or vitality characteristic, or response to an environmental condition to be captured.

Further, some plant health or vitality characteristics, or responses to an environmental condition may contain frequency components having a higher frequency still. Thus in some embodiments a predetermined minimum frequency component of 1 kHz is preferred.

It will, on other hand, be appreciated that some of the transient electrical signals referred to above may have some frequency components with frequencies as low of 1 Hz, or below. As such electrical signal capture from DC is provided for. Further, transient electrical signals may have components with frequencies of at least 10 kHz, and as such a capture bandwidth of at least 10 kHz is provided in some embodiments.

Further, by capturing electrical signals from a plant with an even greater bandwidth, for example a bandwidth of up to 20 kHz, it is possible to capture other higher frequency components. In addition, some components may be present at higher frequencies still, such as, for example, at frequencies of greater than 20 kHz. Moreover, some components may be present at frequencies of up to 125 kHz.

The frequency of signal components which can be captured will depend upon the performance of various system components. The ADC 14, may, for example, determine a maximum sample rate at which an analogue signal can be converted to a digital signal (and thus the maximum sample rate at which subsequent processing in the digital domain can be performed). It will further be appreciated that, according to well-known signal processing theory, it will be required to capture a signal at at least twice its maximum frequency component if it is to be faithfully reconstructed. As such, to capture a signal having a maximum frequency component of 125 kHz, a sampling rate of at least 250 kilo-samples per second (kS/s) should be used.

The ADC may, for example, be configured to have a sampling rate of between 192 and 420 kS/s. Further, an ADC may be configured to run at a frequency which is determined by a standard crystal resonator. The sampling rate of the ADC may, for example, be controlled by a user selection of a power of two division of a standard crystal resonator frequency. It will be appreciated that the sampling frequency can be selected so as to provide for convenient subsequent processing. For example, a sampling rate may be selected which allows for a minimum unit of frequency in FFTs performed on captured data to be any convenient value or whole number amount (e.g. 0.1 Hz).

On the other hand, a sampling rate may be selected based upon the availability of suitable data capture apparatus. The ADC may be provided by a standard computer sound card, providing a sampling rate of, for example, 384 kS/s, with 16-bit amplitude resolution. Such a sound card may be provided with an input which is connected directly to the capture electrode or which is generated by an amplifier connected to the capture electrode.

Similarly, the analogue performance of components (e.g. the amplifier 13, any analogue filters used, the leads 6, 8) may limit the maximum frequency of signal transmitted from the electrodes.

In some instances the relative small size of transient electrical signals, especially in light of a rapidly changing baseline potential may cause difficulty in identifying particular ones of the transient electrical signals discussed above (or indeed other electrical signal components) during periods of increased electrical activity. For example, if insufficient amplitude resolution is provided during digitisation by the ADC 14, it may be impossible to resolve small amplitude features. That is, where a signal capture range is determined so as to accommodate a large amplitude event such as an action potential event, a small perturbation can be represented by only a very small number of distinct voltage levels and can thus become difficult to detect. As such, an ADC having at least 16 bits is preferred, providing 65536 distinct voltage levels, which would, for example, each be just 0.15 mV when using an amplitude range of ±5 V. Such a high resolution allows extremely small signal level fluctuations to be captured across a large amplitude range. Moreover, use of an ADC having greater than 16 bits (e.g.

24 bits—as described above or even 32 bits) provides even more distinct voltage levels allowing both improved voltage resolution and an increased (or at least maintained) amplitude range.

As discussed further above, the use of electromagnetic shielding (e.g. EM shield 9) allows external sources of electromagnetic radiation, such as, for example RF radiation, to be excluded from captured signals. Such shielding provides for improved noise rejection, and thus an improved signal to noise ratio. Without adequate EM shielding, it may be difficult to identify electrical signals which may be indicative of plant health or vitality, which can be seen to have extremely small amplitudes in some cases.

In some embodiments, physical electromagnetic shielding is supplemented or replaced with signal conditioning components. For example, filtering performed in the analogue domain so as to remove unwanted signal components which are caused by electromagnetic interference. Similarly, post processing performed in the digital domain (after conversion within the ADC) may also be performed to remove unwanted signal components which may have been caused by electromagnetic interference.

Leads 6, 8 may be electromagnetically shielded so as to reduce the effect of any electromagnetic interference on the signals sensed by the electrodes 5, 7 as they are passed to the data acquisition module.

As described above, the EM shield 9 may, for example, comprise a Faraday cage which surrounds the whole plant 2. Alternatively, the EM shield 9 may be provided such that the leads 6, 8 themselves are electromagnetically shielded without requiring a Faraday cage. In particular, the leads 6, 8 may be coaxial cables which are arranged to connect each of the electrodes 5, 7 to the plant health monitoring device 1. For the ease of description, the coaxial cable connected to the reference electrode 5 is referred to as a "reference cable" and the coaxial cable connected to the capture electrode 7 is referred to as a "capture cable".

A coaxial cable typically comprises an inner conductor surrounded by a tubular insulating layer, further surrounded by a tubular outer conducting shield. The inner conductors of the coaxial cables act as the leads 6, 8 and are used to transfer signals sensed by the electrodes 5, 7 to the plant health monitoring device 1. The outer conducting shields of the coaxial cables act as the EM shield 9 to shield electromagnetic interference on the signals sensed by the electrodes 5, 7. In this way, less space is required for the plant health monitoring device 1. Of course, it will be appreciated that an EM shield 9 may be provided in addition to the use of coaxial cables as described above.

A standard coaxial cable typically has a capacitance of around 82 pF to 100 pF per metre between its inner conductor and its outer conducting shield. When such a coaxial cable is electrically connected to a plant, for example, as shown in FIG. 1, a low-pass filter is effectively formed by the capacitance of the cable and an output impedance of the plant. The plant may typically have an output impedance of around between 100 k Ohms to 10M Ohms. With this level of output impedance of the plant, the cut-off frequency of such a low-pass filter formed by a one-metre long coaxial cable and the plant may be in the range of around $1{\sim}2{\times}10^2$ Hz to $1{\sim}2{\times}10^4$ Hz.

This cut-off frequency may fall within the frequency range of electrical signals obtained from the plant. Accordingly, there is a risk that components of electrical signals obtained from the plant are attenuated without reaching the plant health monitoring device 1. This may affect the processing results of the plant health monitoring device 1.

In order to compensate for the capacitance of the coaxial cables, a compensation circuit may be provided together with the reference and capture coaxial cables.

In more detail, the capture coaxial cable may be electrically connected to the capture electrode 7 via its inner conductor alone. The inner conductor of the capture cable provides an electrical signal sensed by the capture electrode 7 to the plant health monitoring device 1. The compensation circuit includes a buffer circuit with an amplification factor of '1' for the capture cable. The buffer circuit receives a voltage signal from the inner conductor of the capture cable and outputs a voltage signal to drive the outer conducting shield of the same cable. In this way, the voltage difference between the inner conductor and the outer conducting shield of the capture coaxial cable is maintained at substantially 0 Volt by the buffer circuit. Accordingly, the capacitance of the capture cable does not charge or discharge based upon signal level fluctuations, and any effect on the cutoff frequency is much reduced. As such, the use of a capacitance compensation circuit allows the effective cutoff frequency of the capture cable to be increased to a higher frequency than where no compensation circuit is used.

The reference cable may be connected to the reference electrode 5 via its inner conductor alone, and accordingly may have its own compensation circuit as described above with reference to the capture cable.

Alternatively, the reference cable may be electrically connected to the reference electrode 5 via both of its inner conductor and outer conducting shield. That is, the inner core and the outer conducting shield of the reference cable may be electrically coupled together with a voltage difference of substantially 0 Volt. The outer conducting shield is driven with a voltage of 0 Volt (i.e. ground), to provide a low impedance path for channeling any interference to the ground. The inner conductor of the reference cable, which is also at a voltage of substantially 0 Volt, provides an electrical signal to the plant health monitoring device 1. In this configuration, the reference cable does not require a compensation circuit to compensate for the capacitance of the cable.

In either of these two configurations for the reference cable, the voltage difference between the inner core and the outer conducting shield of the reference cable is substantially zero. Accordingly, the capacitance of the reference cable does charge or discharge during signal acquisition, so its effect to the cutoff frequency may be considered to be insignificant. Thus, transient distortions of the electrical signals obtained from the reference electrode 5 as a result of cable capacitance may be considered to be insignificant.

The buffer circuit may, for example, take the form of a voltage follower. The voltage follower may be an op-amp circuit which has a negative feedback and a voltage gain of '1'.

It will be appreciated that the coaxial cable described here is not limited to a single layer of outer conducting shield. Instead, it may include more than one layer of outer conducting shields for greater bandwidth and rejection of interference.

Further, various types of signal conditioning or filtering may be used (both in the analogue and digital domains) to remove any unwanted signal components, or to enhance other signal components as required. The amplifier 13 is an example of a signal conditioning device which performs signal conditioning in the analogue domain so as to amplify the sensed signals to a level which is suitable for digitisation. It will be appreciated, however, that the use of any particular signal conditioning device is optional.

Once captured, analysis of the electrical signals described above allows for information regarding plant health or vitality characteristics to be determined or for the plant's responses to its environment to be made evident. For example, certain ones of the above described transient electrical signals can be considered to be indicative of particular plant health or vitality characteristics, or a particular measure thereof. For example, the presence of a particular transient electrical signal may be indicative of a particular plant health or vitality characteristic. Similarly, the presence of a combination of transient electrical signals, a frequency of occurrence of a particular transient electrical signal, or a frequency of occurrence of a combination of transient electrical signals may be indicative of a particular plant health or vitality characteristic.

Thus, by capturing electrical activity as described above, and by performing subsequent processing, it is possible to generate a data indicative of a measure of plant health or vitality, for example to monitor the health of a plant or to make evident its response to its environment.

Figure 4:
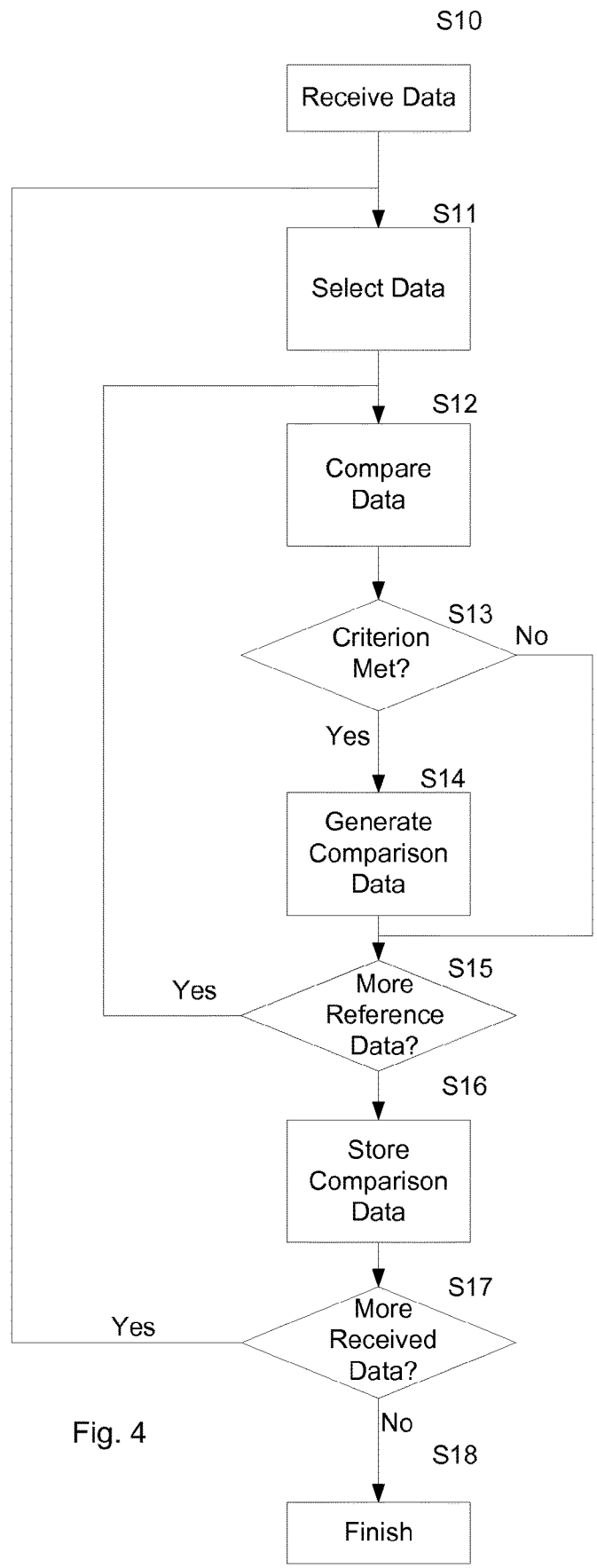
FIG. 4 shows steps of a process carried out by the device of FIG. 1 in more detail.

FIG. 4 shows processing carried out by the CPU 12a to identify and classify particular electrical signals so as to generate a measure of plant health or vitality.

Processing begins at step S10, where data is received by the CPU 12a from the data acquisition module 10. The received data comprises digitised data indicative of the amplitude of the potential difference between the growth medium 3 and the surface of the leaf 2a.

Processing then passes to step S11 where data indicative of the amplitude of the potential difference between the growth medium 3 and the surface of the leaf 2a which satisfies a predetermined criterion is selected. For example, data related to a predetermined time period may be selected from the entirety of the received data. Alternatively, data which was received a particular time, within a particular time range, having particular frequency range, or combination of time and/or frequency ranges, may be selected. It will be appreciated that subsequent processing of data may be performed on data which relates to longer time periods (e.g. hours, days or weeks).

A predetermined period of time may, for example, be a particular ten second time interval. It will of course be appreciated that any convenient time interval can be used.

In other embodiments, the predetermined time period may a shorter time period (e.g. as short as around one second in duration) or a longer timer period (e.g. up to sixty seconds in duration). Indeed, data acquisition and storage may be carried out on a continuous basis, and step S10 may continually receive such data. Processing step S11 provides a degree of selectivity such that subsequent processing can be carried out on a convenient subset of the entirety of the received data.

Processing then passes to step S12 where the selected data is compared against reference data. Such a comparison may, for example, involve the correlation of the selected data with a reference signal in the time domain. The processing performed at step S12 may involve the generation of data indicative of a relationship between the selected data and the reference signal. The data indicative of a relationship between the selected data and the reference signal may, for example, be a correlation coefficient.

In some embodiments the comparison performed at step S12 between the selected data and a reference signal may be performed in the frequency domain. For example, the selected data may be transformed to the frequency domain (e.g. by FFT) and then correlated with reference data which is also in the frequency domain.

Processing then passes to step S13 where it is determined if there is the data contained within the selected data matches the reference signal or signals. Such a determination may, for example, involve determining whether the data indicative of a relationship between the selected data and the reference signal meets a predetermined criterion. For example, a correlation coefficient generated at step S12 may be compared with a correlation threshold, and, if that correlation threshold is exceeded, the criterion is determined to be met.

If the criterion is determined to be met, processing then passes to step S14 where data indicating a positive match between the reference signal and the selected data is generated. The match data may, for example, comprise an indication of the plant specimen from which the data was received at step S10 (e.g. a unique plant identifier), an indication of the particular reference signal with which the comparison has been performed, and a time stamp indicating when the data was acquired from the plant specimen. Processing then passes to step S15.

If the criterion is not determined to be met at step S13, processing instead passes directly to step S15.

At step S15 it is determined whether or not there are further reference signals with which the selected data is to be compared. If there are further reference signals, processing returns to step S12, and steps S12 to S15 are repeated until the selected data has been compared to all of the reference signals. If there are no further reference signals, processing passes to step S16, where the generated data indicating any positive matches between the reference signals and the selected data is stored. The stored data may thus comprise an indication of the plant specimen from which the data was received at step S10 (e.g. a unique plant identifier), an indication of the particular reference signals with which a positive match has been found, and a time stamp indicating when the data was acquired from the plant specimen.

Processing then passes to step S17 where it is determined whether or not there is further received data to be processed. For example, if all of the received data has been analysed then no further processing may be necessary, and processing may terminate at step S18. On the other hand, where there is more received data to be processed, processing returns to step S11 where new data from the received data is selected, and the processing described above from step S11 to S17 is repeated.

The processing described above allows data stored at step S16 to be subsequently used by further processes, either performed by the plant health monitor, or by other processing apparatus. Such further processing can be used to identify particular plant needs (which may, for example, be indicated by the presence or absence of particular reference signals within the received data). By performing further analysis (e.g. statistical analysis) on stored data related to either a single plant specimen, or a plant population, information regarding the health or vitality of those plants can be generated as well as making evident the plants' responses to changes in their environment.

It will further be appreciated that the processing described above may be adapted in a number of ways. For example, data selected at step S11 may be compared to a plurality of different reference signals in series or parallel, rather than repeating steps S12 to S15 a plurality of times. Similarly, the processing described may be performed in parallel on data received from different plant specimens, or on data selected by applying a different selection criterion at step S11.

Further, the processing described above may also include additional processing steps. For example, digital filtering processes may be included over a number of different time periods. Digital filters which are applied may include, for example, finite impulse response (FIR) and infinite impulse response (IIR) filters. One or more notch filters which filter out contributions from well-known electrical interference sources (e.g. power distribution at 50 or 60 Hz) may also be used.

In some embodiments a filter bank comprising a plurality of band pass filters may be used to divide a captured electrical signal into individual frequency bands. Such signal division can be used to allow for multiband analysis and feature characterisation.

Moving averages may also be used to smooth a received electrical signal prior to performing a comparison.

In addition to performing comparisons with reference data, in some embodiments environmental conditions at the time of data acquisition may be taken into account. For example, received data may be correlated with data relating to environmental variables (e.g. a recorded temperature value) so as to identify possible relationships between the acquired data and that variable. Alternatively or additionally acquired data may be normalised with respect to an environmental variable.

Moreover, comparison steps may be augmented or replaced with pattern recognition processes, which may, for example, make use of neural networks to identify reference signals, and to perform comparisons with selected data. In some embodiments, techniques such as principal component analysis may be used to identify similarities or correlations between different data sets (e.g. between selected data and reference data).

In some embodiments, acquired data and/or data relating to environmental variables may be displayed graphically, so as to allow relationships to be examined or analysed visually.

It will be appreciated that while the processing described above may be performed by the CPU 12a, it can also be performed by processors associated with other devices, which may be in some way connected to, or in communication with the CPU 12a. Alternatively, the processing may be performed by a remote computer based upon data captured by the plant health monitoring device 1 and stored for subsequent processing.

In a further alternative, the processing described with reference to FIG. 4 may be performed by several processors.

It will be appreciated that while processing is described as being performed on data received from the data acquisition module 10, processing could instead be performed on data obtained in other ways.

For example the described processing could instead be performed on data retrieved from a storage location (e.g. disc drive 12c) which was previously recorded. That is, as well as, or instead of, the sensed and digitised signals being processed in real time, the digitised signal may be stored (for example in the disc drive 12c). Such storage allows for the captured signal to be further used in a number of ways. For example, subsequent analysis can be carried out on a stored signal. Alternatively, a stored signal can be transmitted to a remote device for analysis. In a further alternative, a stored signal can be re-played to a plant.

A digitised signal may, for example, be stored on local storage associated with the CPU 12a. The local storage may take any suitable form, such as, for example, SD card or similar non-volatile removable memory device, which may be provided in addition to, or as an alternative to the disc drive 12c. Alternatively, a digitised signal may be streamed to a remote device (e.g. a personal computer) or to internet based device (e.g. a cloud based computer) for storage. In some embodiments, a digitised signal may be stored locally until a device is connected which allows transmission. For example, a mobile computing device (e.g. a mobile telephone) may be connected to the plant health monitor device 1 (e.g. via USB or Bluetooth), after which a data connection provided by the mobile computing device is used to transmit the locally stored data to a remote storage location. In a further embodiment, a digitised signal is streamed continuously to a remote computer where the signals are displayed and analysed as required.

Further still, when storing or transmitting a signal, data compression can be used so as to allow data relating to a longer period of time to be stored in a given storage capacity, or transmitted with a given data bandwidth. In some applications, data relating to some regions of time will be compressed more than others. For example, regions of signal which are identified as representing conventional or expected electrical activity may be compressed in preference to regions which are identified as containing unusual electrical activity—allowing more detailed subsequent analysis to be performed on the regions of unusual electrical activity.

Moreover, the nature of signals received from a plant specimen is such that, for significant periods of time only a subset of the whole number of available ADC bits are required to accurately record transient events. For example, only 8-bits of a 24-bit recorded signal may be required to record instantaneous changes, with a 16-bit offset being effectively static within a given time period, It will thus be appreciated that a 16-bit offset value can be stored and transmitted periodically, with a series of 8-bit signals each of which represents an instantaneous voltage level also being transmitted. In this way, the amount of data transmitted or stored can be significantly reduced, allowing more data to be stored on a device, or transferred to a connected device (e.g. via a Bluetooth connection) for storage or display (e.g. in an app on a mobile computing device). In this way, data compression can be used to reduce the storage or connectivity requirements of the plant health monitor device 1.

As described above, plant health or vitality characteristics may, for example, relate to various conditions or stresses of a plant. As such, the plant may generate characteristic signals which provide information related to the environment in which is located and changes in that environment. For example, in use a plant health monitoring device may be configured to indicate to a user when a plant is in need of water. Moreover, such a device may be configured to further indicate to a user when sufficient water has been provided.

More generally, plant health monitoring devices may be configured to alter the way in which a plant is cared for. For example by identifying characteristic electrical activity associated with a plant need, and by performing actions associated with satisfying that need, plant care can be improved. Such actions may include, but are not limited to, alerting a user (e.g. by audible, visible or other means) to the plant need and satisfying the plant need (e.g. by automatically watering the plant, by automatically feeding the plant, automatically increasing or decreasing the humidity, automatically increasing or decreasing light intensity, automatically increasing or decreasing the temperature, automatically applying insecticide, automatically applying fungicide or other automated processes).

In a further example, a plant health monitoring device may be configured to monitor a plant and to identify responses to changing environmental conditions, or environmental conditions which could be changed for the better. When a plant is moved to a new location, which may, for example, have different humidity, temperature or illumination conditions, the response of the plant can be monitored so as to ensure health and vitality of the plant.

Moreover, comparisons can be made between similar plants in different locations, even between plants which are remote from one another. Such a comparison can be made by virtue of a communications network to which the device 1 can be connected, and through which it can communication with another similar device associated with a different plant.

In a further application the electrical signals emitted by a plant can be monitored so as to monitor the effect of illumination on a plant. For example, while the effect of illumination on plant growth may become apparent over the course of several days, the monitoring of electrical activity as described above can provide immediate feedback to a user of the plant's response to the changed illumination conditions. As such, illumination conditions can be adjusted so as to optimise growth at any point in time.

Such monitoring and control of growth conditions can, for example, lead to higher crop yield at relatively low cost. Moreover, crop yield can be maximised by identifying optimal lighting conditions for growth. Further, it will be appreciated that providing artificial illumination may be expensive when applied to a large number of plants. As such, by monitoring electrical signals emitted by plants, it may be possible to determine a cost effective illumination level. That is, artificial or supplemental lighting may be controlled so as to achieve an optimal yield versus electricity cost characteristic.

More generally, the monitoring of electrical activity as described above can provide immediate feedback to a user of the plant's response to the changed environmental conditions, rather than requiring observations to be carried out over days or weeks.

Figure 5:
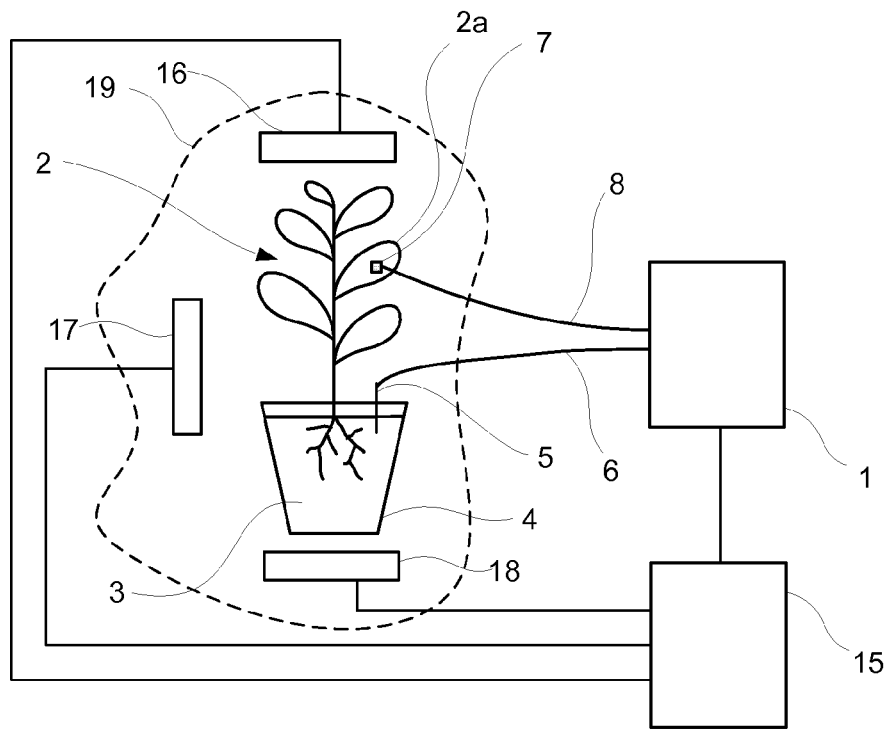
FIG. 5 illustrates an environmental control system including the device shown in FIG. 1.

FIG. 5 shows an environmental control system in which a plant heath monitor device 1 as described above can be used to control the environmental conditions in which a plant is grown. The plant health monitor 1 is arranged to monitor the health of the plant 2, as described above with reference to FIG. 1. In addition to the plant heath monitor device 1, there is also provided an environmental control device 15, a light source 16, an irrigation system 17 and a heat source 18. The environmental control device 15 is arranged to generate a plant control signal. The plant control signal may be used to control the environment 19 in which the plant 2 is grown. Thus, the environmental control device 15 is arranged to control the environment 19 in which the plant 2 is grown. The environmental control device 15 controls various aspects of the environment 19. The environmental control device 15 controls the illumination within the environment 19 by appropriate control of the light source 16. The environmental control device 15 controls the irrigation within the environment 19 by appropriate control of the irrigation system 17. The environmental control device 15 controls the temperature within the environment 19 by appropriate control of the heat source 18.

It will, of course, be appreciated that various combinations of environmental conditions may be controlled by the environmental control device 15. Indeed, other aspects of the plant's environment may be controlled than those described above. For example, in addition to (or instead of) one or more of the light source 16, the irrigation system 17 and the heat source 18, the environmental control device 15 may control a device (or devices) which are arranged to apply fungicide or insecticide to the plant 2, to control the humidity, or to deliver nutrition to the plant 2. Further, one or more of the light source 16, the irrigation system 17 and the heat source 18 may be omitted in some embodiments. More generally, any one or more of the environmental conditions described above, or other environmental conditions, may be controlled by the control device 15.

Figure 6:
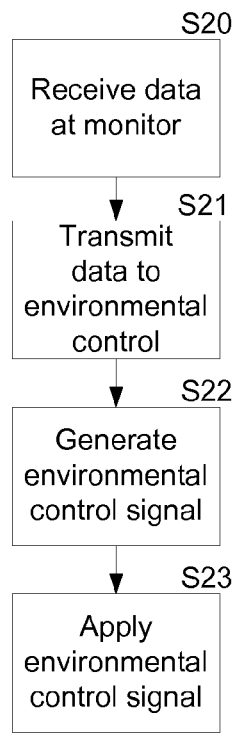
FIG. 6 shows steps of a process carried out by the environmental control system of FIG. 5.

The operation of the environmental control device 15 is now described with reference to FIG. 6. At step S20 a signal is received by the plant health monitor device 1 from the plant 2 and processed so as to generate a measure of plant health or vitality (e.g. as described above with reference to FIG. 4).

Processing then passes to step S21 where the signal is transmitted to the environmental control device 15. Processing then passes to step S22 where the received signal is processed so as to generate an environmental control signal. The environmental control signal is a signal which is used to adjust one or more environmental conditions associated with the plant 2. The environmental control signal may, for example, relate to the control of one or more of illumination, irrigation, insecticide application, fungicide application, temperature, humidity, and nutrition. The environmental control signal is generated based upon a predetermined set of rules which may, for example be based upon historical data relating to plant yield and environmental conditions.

Processing then passes to step S23 where the generated environmental control signal is applied to an environmental control system so as to cause a change in the plant's environment. For example, the generated environmental control signal may cause the light source 16 to increase the intensity of the illumination within the environment 19. The environment control signal may be considered to be an example of a plant control signal.

In an alternative embodiment a plurality of signals are received from a respective plurality of plants. The processing performed at step S22 to generate an environmental control signal is performed on the received plurality of first signals. The processing may, for example, involve performing a statistical analysis of the plurality of signals. For example, a criterion may be required to be met before a predetermined action is performed. For example, if 70% of plants indicate a preference for more light, light intensity may be increased. Alternatively, if 20% of plants indicate the presence of an insect, an insecticide may be released.

It will be appreciated that in any of the processing techniques described above with reference to FIG. 6, processing steps may be repeated at a convenient interval, or based upon a criterion being met.

Further, while it is described above that the signal transmitted to the environmental control device 15 is a measure of plant health or vitality, raw data received from the electrode 7 may instead be transmitted. In such an embodiment, the processing described above with reference to FIG. 4 may be performed by the environmental control device 15. That is, either raw data received from the electrode 7 (and digitised) or data processed as described above may be transmitted from the plant health monitor device 1 to the environmental control device 15. For example, a plant control signal may be generated based upon a comparison between a received signal and reference data indicative of a measure of plant health or vitality characteristic, for example as described above with reference to FIG. 4, and in particular step S13.

Further, raw or processed data may also be transmitted from the plant health monitor device 1 to a storage device (e.g. a server) from which the environmental control device 15 can access the raw or processed data as required.

In some embodiments, a plant may be triggered to switch from a growth mode to a defence mode by an external event, such as, for example, the presence of an aphid on a plant leaf. Alternatively, such a change of mode can be artificially triggered by use of a directed light source, such as a laser. Such a change of mode can be detected by monitoring the release of jasmonic acid within the plant. Such a change of mode can also be detected by monitoring the electrical signal emitted by the plant as described above. Moreover, while a threat (e.g. an aphid) may be present at one leaf of a plant, electrical activity recorded elsewhere on the plant (e.g. at another leaf) may be used to identify the threat. By artificially stimulating such a response, it is possible to capture signals indicative of such a response, and to monitor for such a response occurring. In this way an appropriate action (e.g. release of insecticide) can be triggered when a plant switching to a defence mode is detected.

In addition to monitoring the transition from a first mode to a second mode by monitoring the transient electrical signals, it is also possible to trigger such a state transition by playing such signals back to a plant specimen. For example, a captured electrical signal which is considered to be characteristic of a particular mode (e.g. growth mode) can be played back to a plant specimen to cause the plant to switch from a different mode (e.g. defence mode) to a desirable mode (e.g. growth mode).

A plant health monitor device according to embodiments of the invention can perform further processing to convert captured electrical signals (e.g. transient electrical signals) to audible signals. Such processing allows signals to be interpreted by a user by listening to the audible signal, which can be used as a form of biofeedback signal. A plant health monitor device may comprise a speaker which can, when activated, play audible signals which are in some way indicative of a measure of health, vitality or environmental response of the plant with which the plant health monitor is associated. Such audible signals may be based upon electrical signals acquired from the plant and can simply provide an audible indication of the voltage level at a given point in time. Alternatively, the captured electrical signal can be used to modulate an audio output in amplitude, frequency or phase, or by modifying the waveform in some way so as to synthesise an audio signal which has characteristics which are dependent upon the captured electrical signal.

Further, plant health monitor device according to another embodiment of the invention can perform further processing to convert captured electrical signals into visible signals. Such processing allows signals to be interpreted by a user by observing visible indications, such as, for example, colour changes and/or light flashes which are in some way indicative of a measure of health or vitality of the plant with which the plant health monitor is associated. The visible signals may, for example, be provided by LED indicators or a TFT LCD or LED display. In a similar way to the modulation of audio outputs, visible signals can be modulated in some way so as to have characteristics which are dependent upon the captured electrical signal. Such visible signals can be used as another form of biofeedback, and can be provided directly by the plant health monitor device 1 without the need for additional component or complex processing apparatus.

Further, plant health monitor device as described above can communicate with other similar devices, or with different types of electronic device via one or more communications networks. For example, a plant health monitor device can communicate with a mobile computing device (e.g. a smartphone) so as to allow a user to monitor various aspects of the plant, such as, for example historical plant health or vitality characteristics. An app may be provided for a smartphone which provides an interface for a plant health monitor device.

While the devices and techniques described above are generally associated with a single leaf of a single plant, it will be appreciated that such devices and techniques are equally applicable to a plurality of leaves, possibly of a plurality of plants. For example, devices as described above may be used to monitor a large number of plants, such as samples from throughout a crop. Such monitoring may be used to monitor for healthy crop development, or to alert a grower (e.g. in real time) to a pest attack or infestation. Further, such monitoring can be used to optimise growth conditions so as to maximise a crop yield.

For example, by monitoring electrical signals acquired from plant specimens while varying illumination it is possible to identify optimal illumination conditions.

Alternatively, by logging data received from a plant or crop (e.g. over days, weeks or months), subsequent comparative analysis can allow particular characteristics to be identified. For example, when abnormal growth activity is identified (whether positive or negative), it is possible to examine electrical activity captured at that time, so as to identify electrical signal components which are associated with the abnormal growth activity.

Moreover, it will be appreciated that any of the techniques described herein may be supplemented by further data processing which is performed on data which relates to longer time periods than those related to the characteristic frequencies of the captured signals. That is, data indicative of plant health or vitality, or responses of a plant to environmental changes may be monitored and processed over time periods extended to hours, days, weeks, months and years.

Plant health monitor devices as described above may take any suitable form. For example, in some applications a small, battery powered device might be appropriate (e.g. for use with house plants). On the other hand, in some applications a mains powered device with more significant storage and processing capabilities may be preferred—such as, for example, for performing research, or for monitoring a large number of plants. Moreover, a small, battery powered device for use with house plants may not itself provide any form of user interface or significant data processing capability, and may essentially operate as a data logging device, with user interaction being provided via communication with a further device. On the other hand, a device for research use may allow a user to interact and control the device via a user interface, so as to perform various processing and analysis actions.

Figure 7:
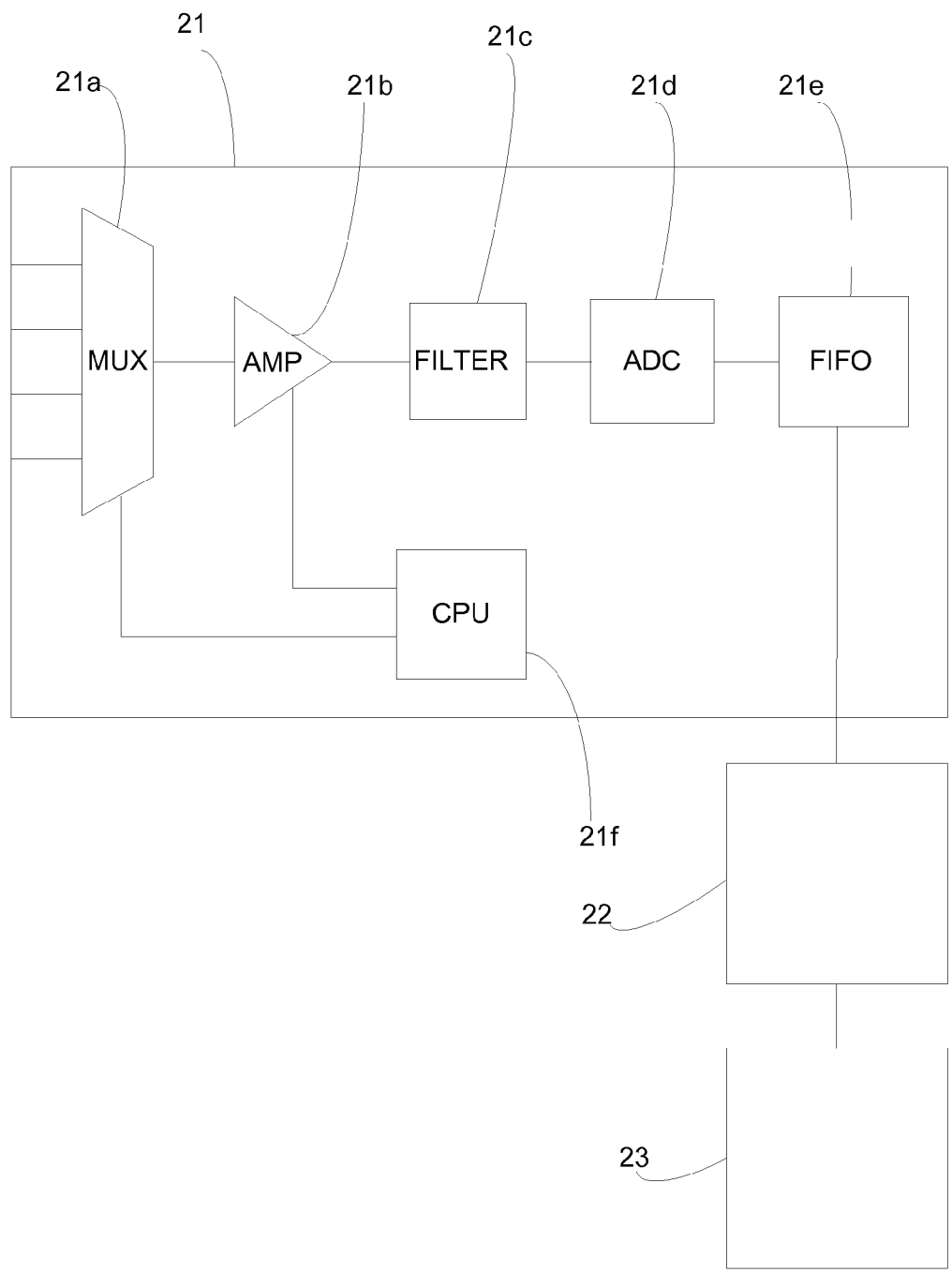
FIG. 7 illustrates a plant health monitoring system according to embodiments of the invention.

A plant health monitoring system 20 is now described with reference to FIG. 7. The plant health monitoring system 20 comprises several components which are also present in the arrangement described above with reference to FIG. 1. However, it will be appreciated that in some embodiments, different functions are performed be different physical components. In the system of FIG. 7, although not shown, a plant 2, electrodes 5, 7, leads 6, 8 are arranged as described above with reference to FIG. 1. The plant health monitoring system 20 comprises a data acquisition module 21, a processing module 22, and an interface device 23.

The data acquisition module 21 comprises signal conditioning and analog-to-digital conversion components. The data acquisition module 21 is connected to the plant 2 via electrodes 5, 7 and leads 6, 8 (not shown). As described above, the leads 6, 8 may be screened so as to reduce the effect of electromagnetic interference on the signal received by the data acquisition module 21.

The data acquisition module 21 comprises an input multiplexor 21a, an amplifier 21b, an anti-aliasing filer 21c, and ADC 21d, a buffer 21e and a controller 21f. The input multiplexor 21a is arranged to select one or a plurality of inputs which is to be passed to the amplifier 21b. The amplifier 21b amplifies the analogue signal before passing it to the anti-aliasing filter 21c. The filtered signal is in turn passed to the ADC 21d, after which the digitised signal is passed to an input of the buffer 21e. The output of the buffer 21e is provided as an output of the data acquisition module 21. Various aspects of control of the data acquisition module 21 (e.g. multiplexor input selection, amplifier gain control) are performed by the controller 21f.

The bandwidth of signals acquired by the data acquisition module 21 may, for example, be in excess of 250 kHz. For example, the ADC 21d may have a sampling rate of 262144 S/s (i.e. $2^{18}$ S/s).

In some embodiments the data acquisition module 21 may comprise separate ground levels for each of the analogue and digital regions, so as to reduce cross-talk between the analogue and digital signals. This may be of particular importance where analogue components have digitally controlled interfaces, such as, for example, digitally switched multiplexors or digitally controlled amplifier gains.

In use the analogue anti-aliasing filter 21c is arranged to condition the sensed and amplified electrical signals before they are digitised by the ADC 21d. That is, the anti-aliasing filter 21c may be arranged to remove analogue signal components at frequencies which would lead to ambiguous signal reconstructions when sampled at the ADC 21d sampling rate.

Given the significant data rate of the ADC, the buffer 21e, which may be a first in first out (FIFO) buffer is provided at an output of the data acquisition module 21. The buffer 21e thus allows for a degree of timing flexibility for data transmission between the data acquisition module 21 and the processing module 22.

The data acquisition module 21 is arranged to transmit data in the form of digitised signals to the processing module 22. The data transmission may, for example, be carried out using a UDP data link. Such a data link may allow for data to be transferred at a rate of, for example, 10 Mbps over a physical link such as, for example, an Ethernet link (e.g. Fast Ethernet using an optical link). Such an Ethernet link allows digitised data to be transferred from the data acquisition module 21 while simultaneously allowing control and configuration data to be to be transferred to the data acquisition module 21 using, for example, a TCP/IP link. Such data transfers may be possible using conventional 100 Mbps or 1000 Mbps Ethernet links. Such control and configuration data may be passed to the controller 21f.

The processing module 22 is capable of receiving digitised signals from the data acquisition module 21, and performing processing on those signals. The processing module comprises a processor and other components (e.g. memory, storage, bus interconnect, interfaces) as required to perform the described processing. It will be appreciated that the processing module 22 may take the form of a conventional computer and may, for example, be substantially as described above with reference to FIG. 2 (albeit without the inclusion of the data acquisition module 10). The processing module 22 may be provided with a plurality of processing cores (e.g. four cores), so as to increase processing power.

Further, the processing module 22 may not have a local user interface, and may instead be operated remotely by the interface device 23. The interface device 23 may, for example, be a conventional personal computer, and may be arranged to control and interact with one or more processing modules. It will, of course, be appreciated that the interface device 23 may be provided remotely from the processing module, and may be connected via any convenient communications protocol.

Processing performed by the processing module 22 on the received digitised signal is now described with reference to FIG. 8. At block B1 the received digitised signal is formed into convenient blocks for subsequent processing. The blocks may each comprise a temporal segment of the received digitised signal. For example, each temporal segment may correspond to 1 second of the digitised signal. In the system described above, each 1 second temporal segment comprises 262144 samples.

It will be appreciated that a temporal segment can be selected to have any convenient duration. However, the longer the duration of the temporal segment, the longer the acquisition process (and subsequent processing) takes. Conversely, the longer the duration of the temporal segment, the better the possible frequency resolution in subsequent analysis. As such, a compromise should be reached between temporal and frequency requirements for each application area.

Once the signal has been formed into convenient blocks (i.e. temporal segments), each segment is provided sequentially to block B2, which performs a Fast Fourier Transform (FFT). Given the real (i.e. not complex) nature of the digitised signal, it will be appreciated that only positive outputs of the FFT will be used in subsequent processing. This fact can be used to improve the efficiency of processing. For example, a second segment of real data may be processed simultaneously with a first segment, and subsequently unpacked, allowing a reduction in the time required to process, on average, each segment.

The output of the FFT block B2 is a spectrum which represents the amplitude of signal components at various frequencies within the transformed temporal segment. A segment of 1 second in duration having 262144 samples may be transformed into a spectrum having 262144 amplitude values, each representing a different frequency.

It will be appreciated, of course, that different sampling rates, segment lengths, or frequency resolutions may be used. It will further be appreciated that in order to allow real time processing, the processing module 22 should provide sufficient processing power to enable the FFT (and other processes described herein) to be performed in a shorter time period than the length of the block. Further, the use of a multi-core processor allows multiple threads of processing to be performed simultaneously.

The output of the FFT block B2 is passed simultaneously to a running statistics block B3 and a current feature vector block B4.

The running statistics block B3 computes a continuous average and standard deviation of the frequency spectrum. That is, the running statistics block B3 computes the mean of all previous amplitudes values (including the present value) for each frequency component, and also a standard deviation of all previous amplitude values (including the present value) for each frequency component within the FFT spectrum. This processing allows the running statistics block to effectively maintain a memory of previous FFT spectra, and to interpret the current FFT spectrum in light of that memory (as described in more detail below). The computed mean and standard deviation values may be based upon a predetermined number of previous frequency strectra, In some embodiments a circular buffer may be used having the predetermined number of buffer elements. Once the circular buffer is fully populated, new entries will replace the earliest entries in the buffer, ensuring that the buffer contents represented the most recent predetermined number of spectra (and thus the most recent predetermined number of temporal segments). Given the real nature of the digitised signal, any negative frequency components are discarded at this point, as they will be simply a reflection of the positive components.

Figure 9:
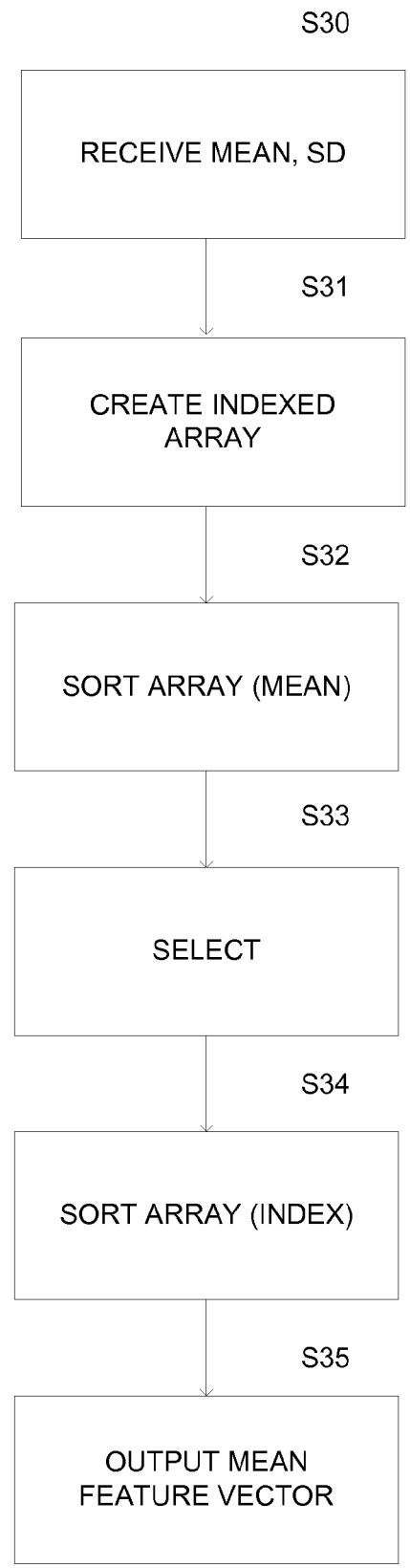
FIG. 9 shows steps of a process carried out by the system of FIG. 7 in more detail.

The computed mean and standard deviation spectra are passed to the mean feature vector block B5. The mean feature vector block B5 performs processing as described with reference to FIG. 9.

Processing starts at step S30 where the mean and standard deviation spectra are received by the mean feature vector block B5. The mean feature vector block B5 then creates, at step S31, an indexed array comprising the mean amplitude values, the standard deviation values and an index. The index may, for example, be a simple index which allows the identification of the frequency corresponding to each of the mean and standard deviation values.

Processing then passes to step S32 where the indexed array is sorted based upon the mean amplitude values. That is, a sorted array is generated in which the entry having the highest mean amplitude is provided first, followed by the second highest mean amplitude value, and so on. The index of the sorted array thus provides an indication of the frequencies having the highest average amplitude in the received spectra.

Processing then passes to step S33 where the array is truncated. During the truncation least significant values within the sorted array are discarded with the most significant values being retained. The number of values retained in the sorted array depends on each application and the level of data compression, and feature resolution required. For example, in an embodiment having 131072 different frequency components (positive frequencies only from 262144 positive and negative frequencies), the most significant 50 values may be retained.

Processing then passes to step S34 where the truncated array is again sorted based upon the index values to create a mean feature vector. That is, a mean feature vector is generated in which the entries are ordered based upon their index value, and thus ordered based upon the frequency to which the amplitude values correspond. The mean feature vector contains the average amplitude and standard deviation of each of the (e.g. 50) most significant spectral features within the digitised signal, regardless of the frequency of those features. That is, no prior knowledge of the significant frequencies is required for the mean feature vector to be generated. After a settling period, the mean feature vector (which is based upon historical FFT spectra), will provide a relatively stable indication of which frequencies contain the majority of digitised signal power. The mean feature vector is provided, at step S35, to the current feature vector block B4.

The processing performed by the current feature vector block B4 is described with reference to FIG. 10. At step S40 the current feature vector block B4 receives as inputs FFT data which represents the amplitude of signal components at various frequencies within the transformed temporal segment, and the mean feature vector.

Processing passes to step S41 where the current feature vector block B4 effectively filters the current FFT spectrum so as to extract only the amplitudes which correspond to the frequencies contained in the mean feature vector. Amplitudes contained within the current FFT spectrum which do not correspond to one of the frequencies contained within the mean feature vector are discarded.

Processing then passes to step S42 where the amplitudes of the various components of the current FFT spectrum are normalised so as to allow comparisons to be more easily performed. This normalisation may, for example, be accomplished by a normalisation process known as hyper-spherization. The hyper-spherization process involves subtracting the mean value for each spectral component (as contained in the mean feature vector) from each component of the filtered current FFT spectrum. The result of this subtraction is a zero centred value. The result of the subtraction is then divided by the respective standard deviation value (as also contained in the mean feature vector) so as to produce a set of values each having, over time, unity standard deviation. This resulting vector forms a current feature vector and has a long term statistical distribution with a zero centred mean and unity standard distribution.

The normalisation method described above thus allows the amplitude values to be scaled and weighted such that any change in the amplitude of any of the signal components represented by those amplitude values generates a scaled modification in the current feature vector. For example, if a first frequency component has a mean amplitude of say 700 (arbitrary units), and changes by 70, and a second frequency component has a mean amplitude of 0.07, and changes by 0.007, both cause a change in the amplitude of their respective features in the current feature vector by exactly the same amount.

This process reduces the extent that changes in very large amplitude frequency components swamp changes in smaller amplitude frequency components. It is noted that smaller amplitude frequency components may contain important information regarding the health, vitality or environmental response of a plant. This normalisation or equalization process (hyper-spherization) improves the suitability of the resulting current feature vector for post processing using a neural network, which can be taught to look for a predetermined characteristic.

The current feature vector is then provided, at step S43, to a transmission block B6. The transmission block B6 simply transmits the current feature vector to the interface device 23. The current feature vector which is transmitted to the interface device comprises a significant reduction in the volume of data received by the processing module 22 from the data acquisition module 21. For example, in the example described above, a data stream comprising 262144 samples each second is reduced to a current feature vector comprising just 50 parameters each second, or 100 parameters if index values are also included. This represents a significant reduction in the data transmission requirements, and allows a relatively slow data connection to be used. For example, a data link capable of supporting just 3200 bytes per second is likely to be capable of transferring such a small volume of data.

The interface device 23 may be further arranged to perform additional processing on the received current feature vectors (which may be received every second). For example, characteristic features relating to the monitored plant 2 may be identified by processing performed on the current feature vectors. In some embodiments neural networks may be trained to recognise features within current feature vectors which are indicative of certain plant health or vitality conditions, or changes in a plant's environment or condition (as discussed in more detail above). Such a process may be left running on an interface device indefinitely, allowing an alert to be raised, for example, when an occurrence of a particular event is identified.

It will, of course, be appreciated, that any of the processing described above with reference to the data acquisition module 21, the processing module 22, and the interface device 23 may be performed by different physical entities as required. For example, the function of the block former B1, may instead be performed by components of the data acquisition module 21, allowing divided temporal segments to be transmitted to the processing module 22 rather than a continuous steam of digitised data. Similarly, various functions described above may be performed by a single device, or a plurality of separate devices, as required by each particular application.

Some examples of data captured and processed by a plant heath monitor system as described above will now be described.

Data was captured using a data acquisition module 21 is described above from leaves of a *Coleus* plant under varying illumination conditions.

Experiments were conducted on *Coleus* plants in an arrangement as described above with reference to FIG. 1. The illumination level was measured using a PAR meter. Initially the lighting was provided using a mixture of incandescent and LED lighting arranged above the plant 2 which illuminated the plant 2 through an array of 2 mm holes spaced at 3 mm in a roof of a chamber in which the plant 2 was located. The initial photosynthetically active radiation (PAR) illumination level reached was 200 micromoles per square metre per second. The plant was allowed to reach equilibrium over a period of 15 minutes and then the illumination was reduced to less than 10 micromoles per square metre per second. The response of the plant was recorded for a period of 30 seconds before the illumination was reduced and the recording was continued for a period of 30 seconds after the illumination was reduced.

Figure 11:
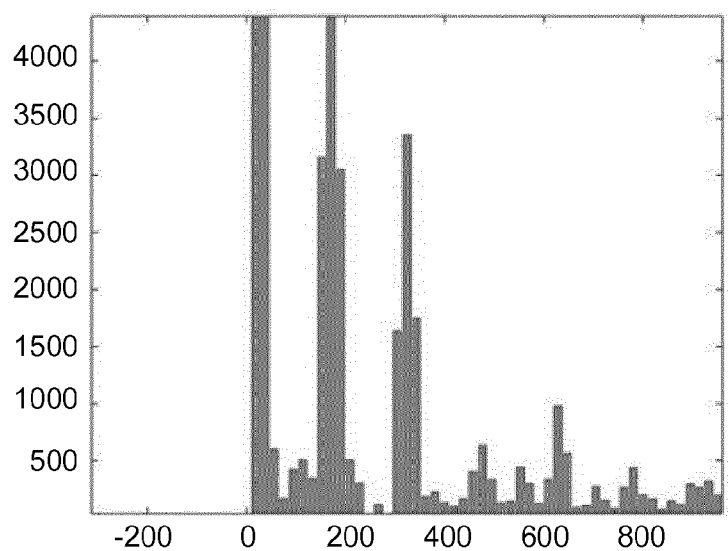
FIG. 11 shows data generated by the system of FIG. 7.

FIG. 11 shows a section of a plot of FFT spectrum components which represent the relative strength of signal components at a variety of frequencies. It can be seen that the amplitude of several components (in the y-axis) is greater than can be shown on the axis provided. Similarly, many components are not shown (in the x-axis). Each of the frequency components contains information relating to a band of frequencies of approximately 20 Hz in width.

While specific conclusions cannot be reached from visual inspection of the plotted data, it can be seen that the signal sensed from the *Coleus* plant does contain information at a variety of signal frequencies.

During processing of data from the *Coleus* plant (which is performed as described above with reference to FIGS. 8 to 10), a temporal segment of around 0.05 seconds was selected, which corresponded to $2^{20}$ samples per block (using a data sampling rate of 100 Ms/s). Performing an FFT on this data enables a frequency resolution of around 20 Hz to be achieved, with the FFT generating around 1000000 frequency components. As described above, half of these components are discarded as only real data is included in the digitised signal.

Figure 8:
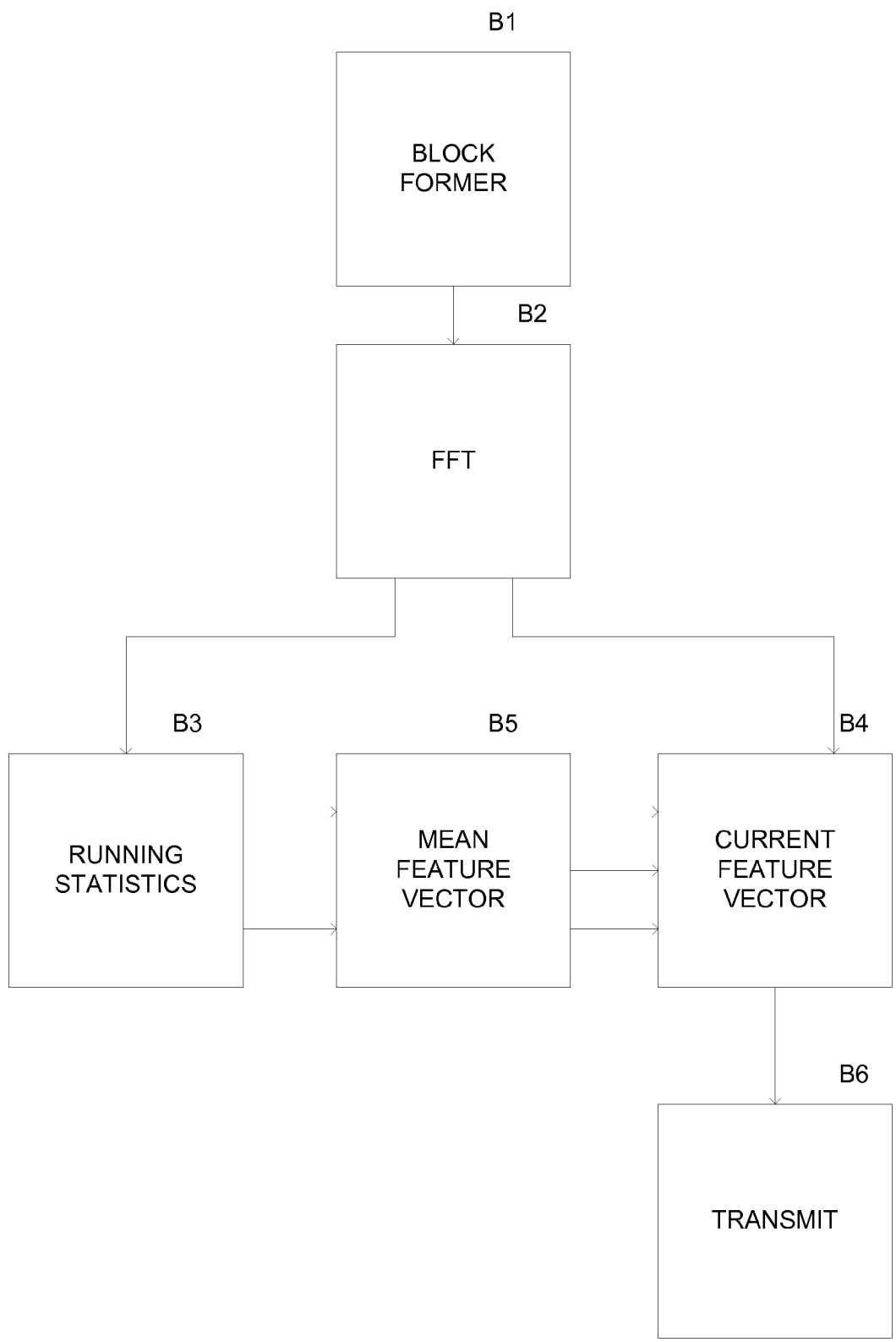
FIG. 8 illustrates processing carried out by the plant health monitoring system of FIG. 7.

Mean values and standard deviations were calculated for each of the remaining frequency components (see FIG. 8, block B3). The frequency components were then arranged in an indexed array (step S31, FIG. 9), sorted (step S32), truncated (step S33) and re-sorted (step S34) so as to select only the 50 frequency components which have the largest mean amplitude within the FFT spectrum.

Figure 10:
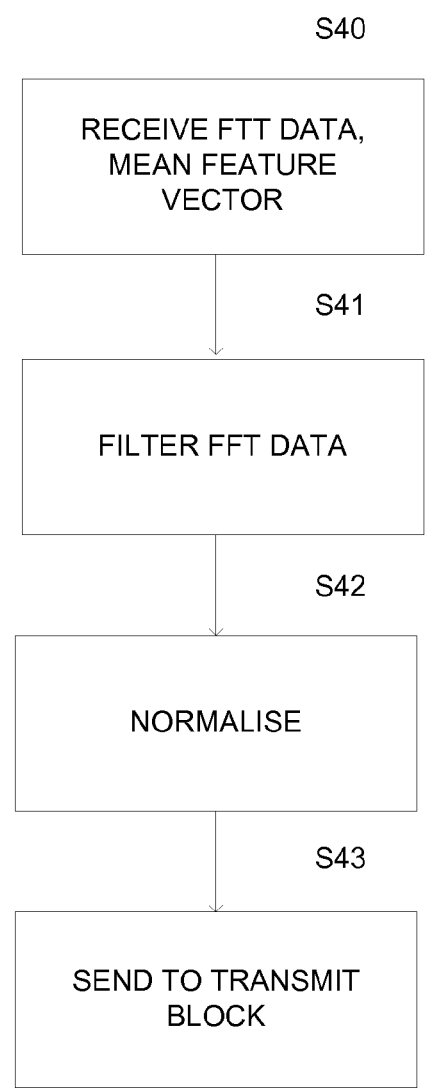
FIG. 10 shows steps of a process carried out by the system of FIG. 7 in more detail.

The current frequency components are then processed (as shown in FIG. 10) in combination with the mean feature vector so as to select only the 50 frequency components which correspond to have the largest mean amplitude within the historical FFT spectrum. Further, the selected frequency components are normalised as described at step S42.

In this case, the resulting data output contains just 50 amplitude values and 50 index values, representing a data reduction ratio of approximately 10000:1. It will further be appreciated that this processing does not require any prior knowledge of the actual frequency distribution contained within signals received from a plant, and automatically extracts the most significant spectral features, without use of conventional (i.e. frequency specific) filtering techniques.

Sample blocks of data (temporal segments) which were gathered when the *Coleus* plant was in dark conditions and when the *Coleus* plant was illuminated were both processed as described above using data relating to both dark and illuminated conditions to provide inputs to the mean feature vector, and to generate a current feature vector. Data was captured simultaneously from two different leaves of a single plant.

Figure 12A:
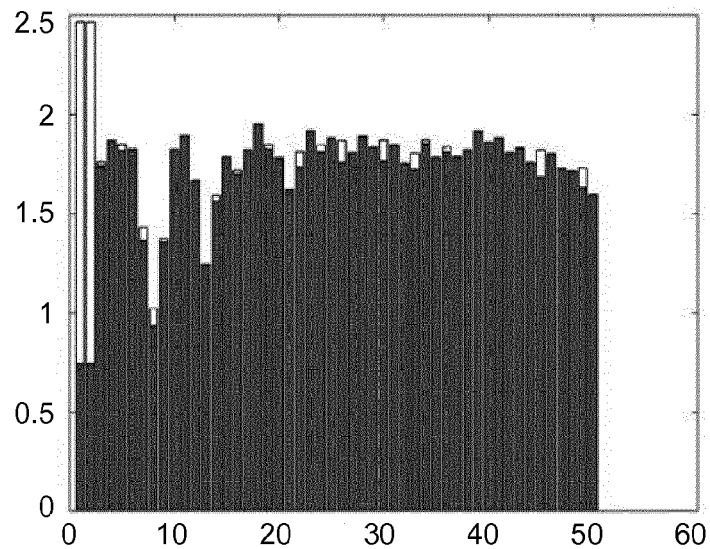
FIGS. 12a and 12b show data generated by the system of FIG. 7.

FIG. 12a shows a comparative plot of a current feature vector based upon data collected during both dark and illuminated conditions (illuminated is shown as unfilled bars, dark is shown as filled bars) from a first leaf. The vertical axis shows the normalised magnitude of the components of the current feature vector (i.e. the most significant spectral features), while the horizontal axis represents the components of the current feature vector, with the lowest frequency components at the left hand side. It can be seen that the lowest two frequency components of the current feature vector exhibit a significant difference between dark and illuminated conditions. It will be appreciated that the plotted current feature vector does not contain information about which frequencies are represented by each of the frequency components on the horizontal axis. However, the order in which the components appear represents increasing frequency (left to right).

Figure 12B:
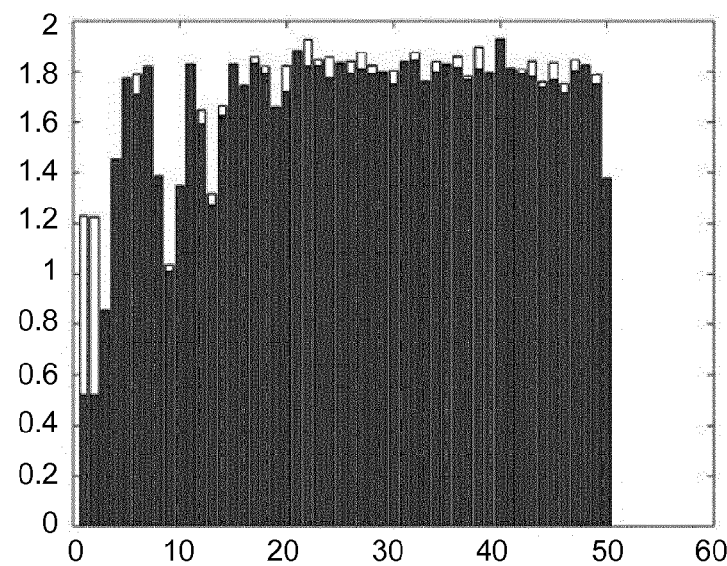

FIG. 12b shows a further comparative plot of a current feature vector based upon data collected during both dark and illuminated conditions (illuminated is shown as unfilled bars, dark is shown as filled bars) from a second leaf. The vertical axis shows the normalised magnitude of the components of the current feature vector (i.e. the most significant spectral features), while the horizontal axis represents the components of the current feature vector, with the lowest frequency components at the left hand side. Again, it can be seen that the lowest two frequency components of the current feature vector exhibit a significant difference between dark and illuminated conditions.

It will thus be appreciated that the data collected from the *Coleus* plant can be processed as described above to generate data indicative of a change in the environment of the plant (i.e. illumination). Indeed, signals captured from distinct leaves exhibit differences in the generated current feature vector which can be related to the change in environmental conditions. Such processing may be used, for example in combination with the environmental control system described with reference to FIG. 5, to control environmental conditions of the plant.

Some further examples of data captured by a plant heath monitoring devices and systems as described above and the analysis thereof will now be described.

Figure 13A:
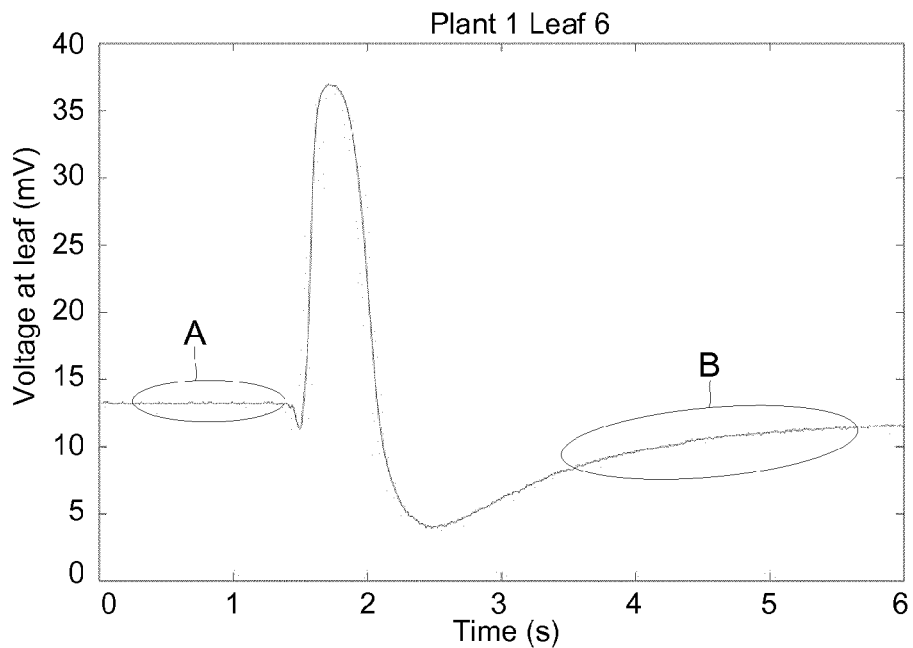
FIGS. 13a and 13b show a signal captured by the device of FIG. 1.

FIG. 13a shows an electrical signal captured from a Venus flytrap by electrodes such as electrodes 5, 7 during an action potential event, which is triggered by mechanical stimulation (i.e. by touching a trigger hair). The electrical signal is converted using a 14-bit ADC, with a sampling rate of 100 mega samples per second (MS/s). The electrical signal is captured using a Spectrum SPA 1412 preamplifier manufactured by Spectrum Systementwicklung Microelectronic GmbH, Germany. The preamplifier was set to a voltage gain of 100. The amplifier has a frequency range of DC to 200 MHz, 1 megohm input impedance, and 50 ohm output impedance. An input bias current of 10 pico-amps was also used.

The electrical signal can be seen to exhibit a stable baseline voltage of around 13 mV for around 1.5 seconds before an action potential event is triggered, this is identified as region A. This event involves a small dip (of around 1.5 mV, at time 1.6 s) before a large and rapid rise in potential to around 36 mV (peak at time 1.8 s), which is followed by a drop to around 4 mV (minimum at time 2.4 s). The potential then gradually increases towards the original baseline over the remaining 3.6 s of the illustrated signal—which period is identified as region B. The peak (1.8 s) and minimum (2.4 s) show a potential change of around 35 mV in around 0.6 s.

Figure 13B:
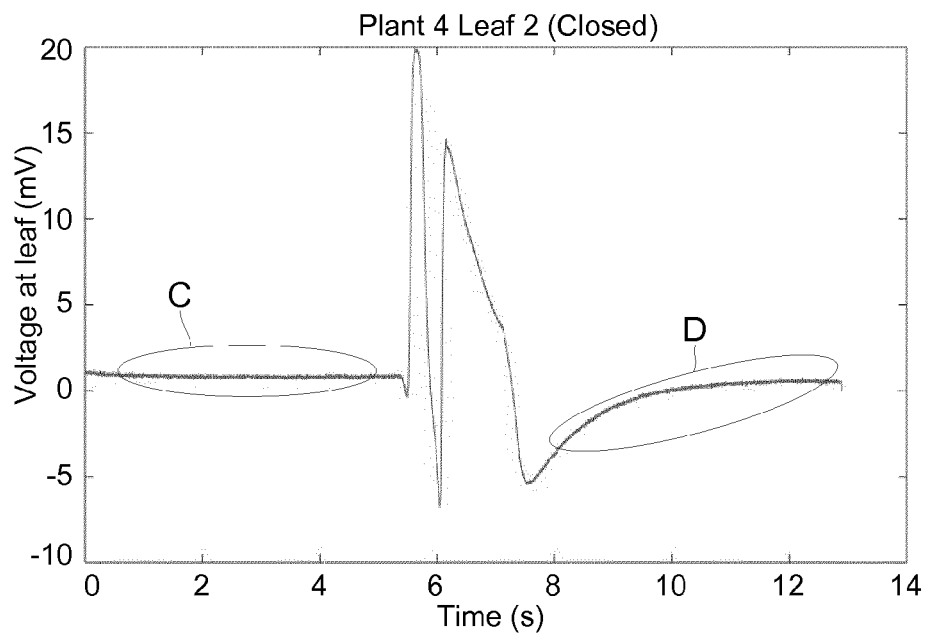

FIG. 13b shows a further electrical signal captured from a Venus flytrap by electrodes such as electrodes 5, 7 during an action potential event. The electrical signal is again converted using a 14-bit ADC, with a sampling rate of 100 MS/s. The electrical signal can be seen to exhibit a stable baseline voltage of around 1 mV for around 5.5 seconds before an action potential event is triggered (identified as region C). This event involves a small dip (of around 1.5 mV, at time 5.6 s) before a large and rapid rise in potential to around 20 mV (peak at time 5.7 s), which is followed by a drop to around −7 mV (minimum at time 6 s). The potential then rapidly rises towards a second peak of around 14 mV (at time 6.2 s) before falling to a second minimum of around −5 mV at time 7.5 s. The amplitude then gradually increases towards the original baseline over the remaining 5 s of the illustrated signal—which period is identified as region D. The peaks (5.7 and 6.2 s) and minimums (6 and 7.5 s) show potential changes of around up to 26 mV over time periods of around 0.3 s.

This behaviour illustrated in FIGS. 13a and 13b is considered normal in 'sensitive' plants such as a Venus flytrap, and shows the variation of electrical potential at the surface of a leaf before, during, and after action potential events.

Figure 14:
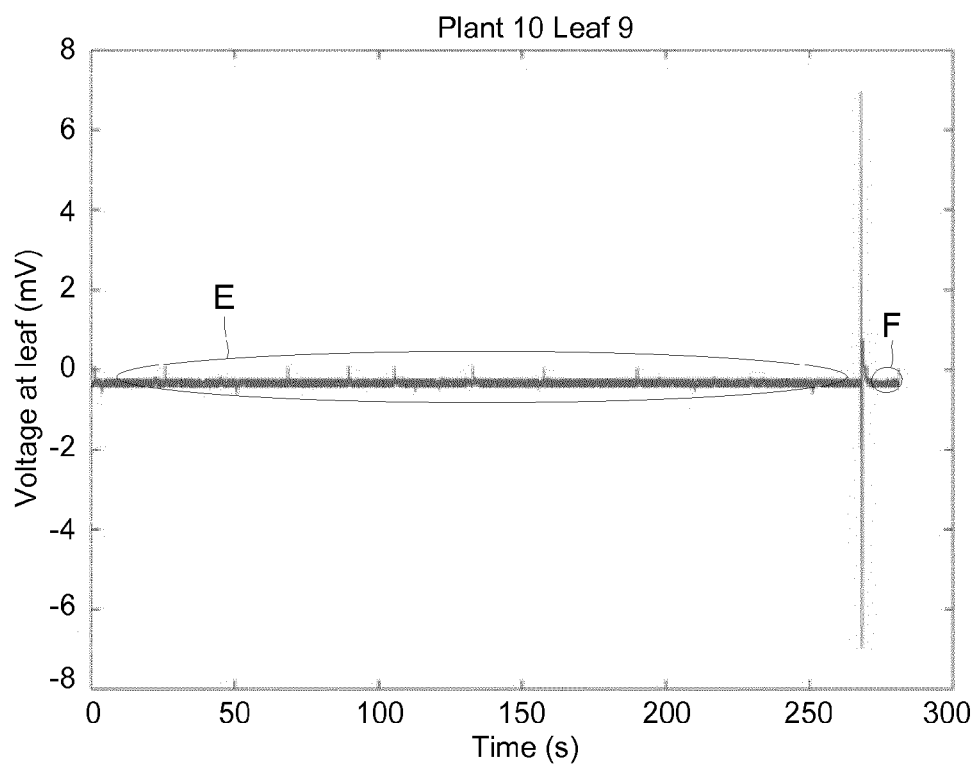
FIG. 14 shows a further signal captured by the device of FIG. 1.

FIG. 14 shows a yet further electrical signal captured from a Venus flytrap by electrodes such as electrodes 5, 7 during a further action potential event. The electrical signal is converted using a 14-bit ADC, with a sampling rate of 1 MS/s. The electrical signal can be seen to exhibit a relatively stable baseline voltage of around −0.4 mV for around 265 seconds before an action potential event is triggered. This action potential event involves a rapid rise in potential to around 7 mV, which is followed by a drop to around −7 mV. The amplitude then gradually returns to the original baseline over the remaining 20 s of the illustrated signal.

However, in contrast to the waveforms shown in FIGS. 13a and 13b, the waveform shown in FIG. 14 also shows a number of small perturbations during the relatively stable period before the action potential event is triggered. Some of the small perturbations occur during the time period can be identified in a region E. It will be appreciated that these small perturbations cannot be readily characterised at the temporal or amplitude resolution shown in FIG. 14. However, when examined in more detail, it has been realised that these smaller perturbations are evidence of transient electrical signals which are also present, rather than being a result of noise or measurement artefacts. Further, during the regions of relative inactivity following action potential event, such as a region F, further perturbations are observed.

That is, in addition to the significant (i.e. tens of mV) potential fluctuations observed during an action potential event, these smaller perturbations are transient electrical signals which can be considered to be indicative of a state of a plants health or vitality.

Figure 15:
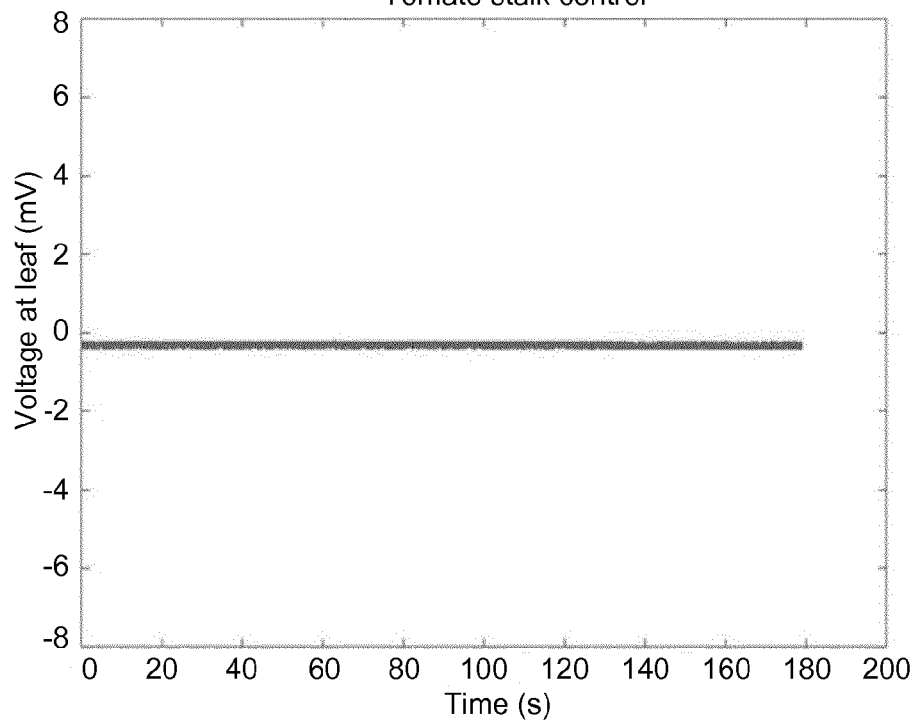
FIG. 15 shows a further signal captured by the device of FIG. 1.

By way of comparative example, FIG. 15 shows a control electrical signal captured from a tomato stalk using the experimental setup used to capture the data illustrated in FIG. 14. As can be seen from a comparison of FIGS. 14 and 15, the perturbations seen in FIG. 14 are not present in the data plotted in FIG. 15, and thus are not considered to be likely to have been caused by external interference or contamination from external sources (which external sources would be common to both capture environments).

The region E preceding the action potential event in FIG. 14 has been analysed in more detail and found to contain around forty such perturbations. That is, during a period of around 265 seconds, a perturbation, or transient electrical signal, occurred approximately every six seconds.

Each of the various perturbations, when examined in more detail, generally appears to correspond to one of a small number of characteristic waveforms. That is, each of the perturbations is an occurrence of a transient electrical signal having a predetermined and repeatable characteristic waveform. FIGS. 16a to 16f shown simplified waveforms representing each of six different transient electrical signals identified as being present during the region E preceding the action potential event in FIG. 14. The transient electrical signals typically have a duration of the order of 0.025 to 2 seconds, and an amplitude of less than 1 mV (although some are longer or shorter lasting, while some have a larger amplitude).

Figure 16A:
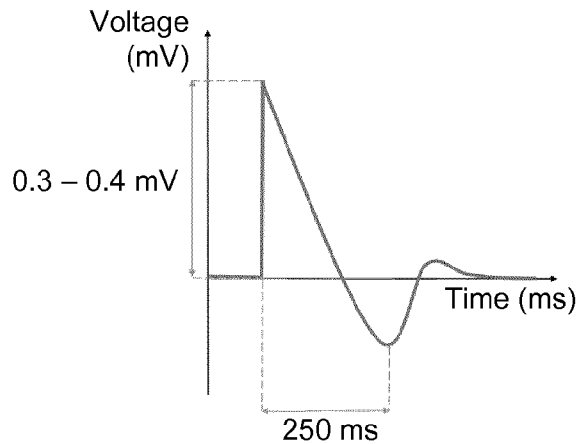
FIGS. 16a to 16f show representations of portions of a signal of FIG. 14.

FIG. 16a shows a simplified representation of a first transient electrical signal which comprises an abrupt rise of about 0.3-0.4 mV in potential from a baseline, followed by a gradual (but approximately linear, or ramp-like) decrease over about 250 ms to a minimum value which is below the baseline. The amplitude then returns to the baseline value after a small positive overshoot.

Figure 16B:
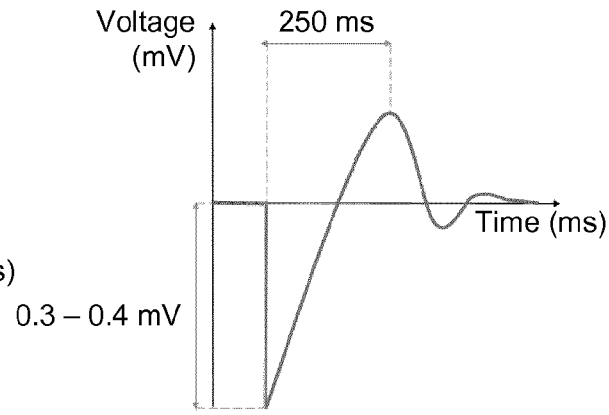

FIG. 16b shows a simplified representation of a second transient electrical signal which comprises an abrupt fall of about 0.3-0.4 mV in potential, followed by a gradual (but approximately linear, or ramp-like) increase over about 250 ms to a maximum value which is above the baseline. The amplitude then returns to the baseline value after a small negative overshoot.

Figure 16C:
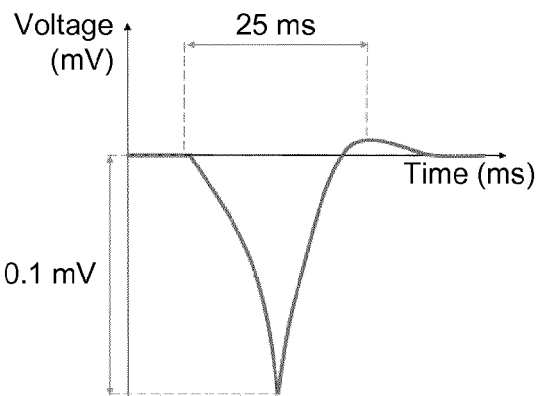

FIG. 16c shows a simplified representation of a third transient electrical signal which comprises an abrupt drop of about 0.1 mV in potential, followed by a correspondingly abrupt rise of the same magnitude returning to the baseline. The third transient electrical signal has a duration of about 25 ms (i.e. each of the rise and fall last for approximately 12.5 ms).

Figure 16D:
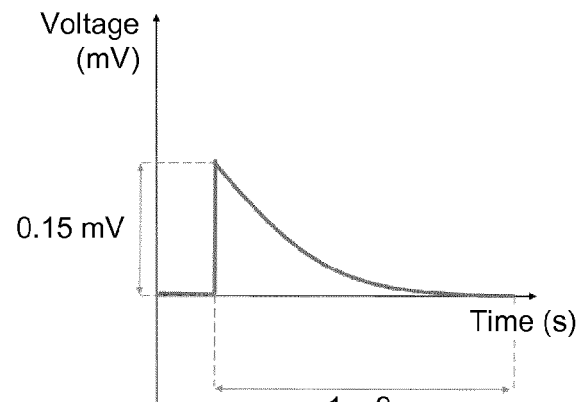

FIG. 16d shows a simplified representation of a fourth transient electrical signal which comprises an abrupt rise of about 0.15 mV in potential, followed by a gradual (but approximately linear, or ramp-like) decrease over about 1-2 s to the baseline.

Figure 16E:
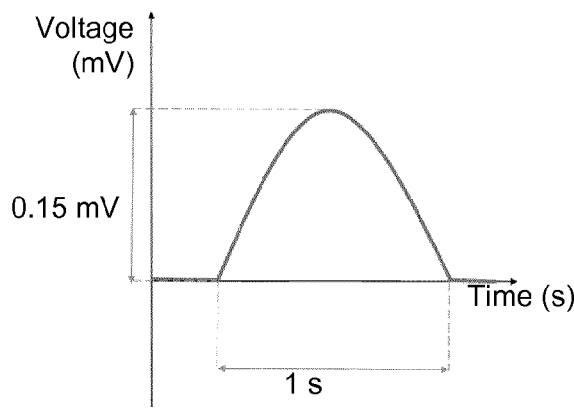

FIG. 16e shows a simplified representation of a fifth transient electrical signal which comprises a hump of about 0.15 mV in potential having a duration of about 1 s.

Figure 16F:
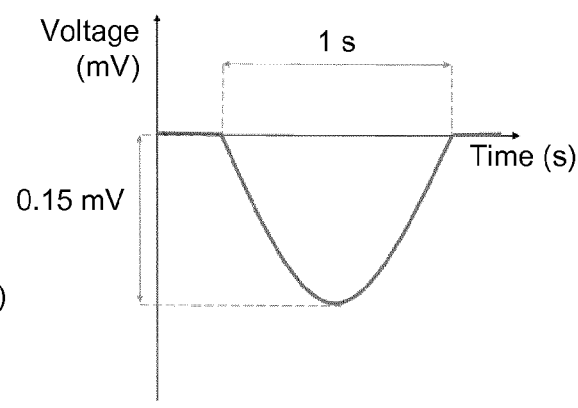

FIG. 16f shows a simplified representation of a sixth transient electrical signal which is an inversion of the fifth transient electrical signal, and comprises a dip of about 0.1 mV in potential having a duration of about 1 s.

Many of the perturbations, or transient electrical signals, identified during the period region E preceding the action potential event in FIG. 14 can be classified as being an occurrence of one of the first to sixth transient electrical signals. As such, the first to sixth transient electrical signals as illustrated in FIGS. 16*a* to 16*f* can be considered to be reference signals with which portions of a captured electrical signal can be compared so as to identify the occurrence of particular ones of the first to sixth transient electrical signals. It will, of course, be appreciated that the first to sixth transient electrical signals are examples of transient electrical signals, and are not a complete set of transient electrical signals. Further, it will also be appreciated that the first to sixth transient electrical signals are representative reference signals, and that occurrences of the various transient electrical signals in a plant specimen may not correspond exactly to the reference signals in amplitude, duration, or waveform shape.

The region following the action potential event in FIG. 14 (identified as region F) has also been analysed in more detail and found to contain further perturbations occurring at an increased rate of around ten or more perturbations per second (as opposed to one every six seconds prior to the action potential event). Thus, it seems that the plant is caused (by the action potential or some other contemporaneous event) to enter a state of high electrical signal activity.

Further, even during regions of relative inactivity, such as regions A-D on the plots of FIG. 13*a*, 13*b*, perturbations which were previously considered to be noise, can be examined in more detail and shown to be evidence of low amplitude higher frequency electrical signals (rather than noise).

While particular transient electrical signals are identifiable, as described above with reference to FIGS. 16*a* to 16*f*, the captured electrical signals may also contain additional components which are further indicative of a state of the plant. That is, in addition to the transient electrical signals, which are typically of the order of 0.025 to 2.5 seconds in duration, further electrical signal components having longer or shorter characteristic signal durations may be present. It will be appreciated, of course, that transient electrical signals may be observed with different durations or frequencies.

While the signal capture and processing described above is generally associated with a particular leaf exhibiting transient electrical activity when stimulated so as to close, different leaves on a plant were also examined during closure activity. That is, a first leaf 2*a* was monitored for electrical activity, as described above, while a different leaf of the plant 2 was stimulated so as to close. During this monitoring electrical activity was captured with a sampling rate of 1 MS/s, and with an additional high gain amplifier used to provide a signal with an amplitude which can be readily detected.

Figure 17A:
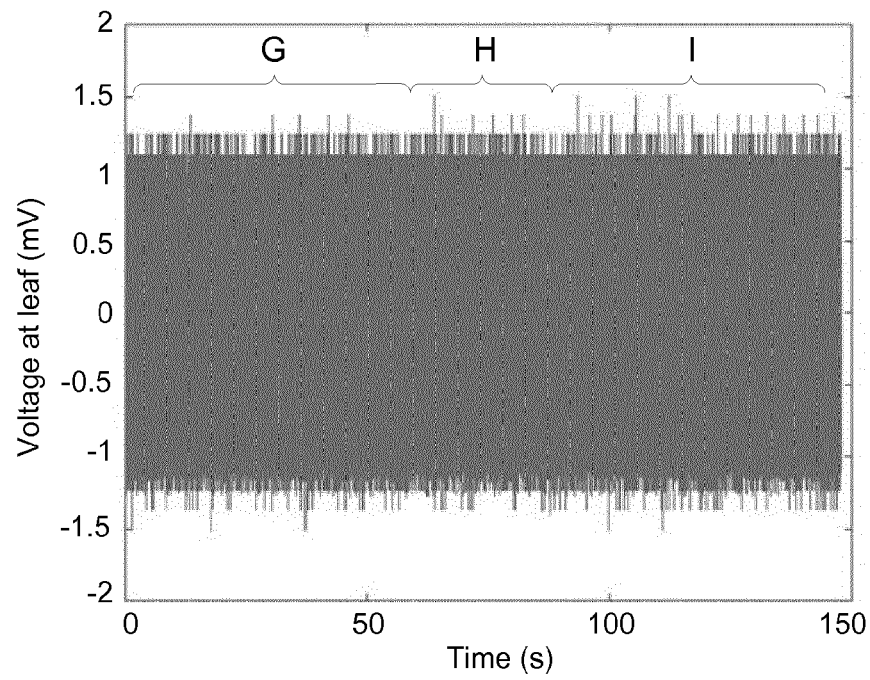
FIGS. 17a and 17b show a further signal captured by the device of FIG. 1.

FIG. 17*a* shows an electrical signal captured from the leaf 2*a* during such activity. During a first period G of the waveform, there is no mechanical stimulation of the plant 2. During a second period H of the waveform, mechanical stimulation is used to attempt to cause leaves of the plant 2 other than the monitored leaf 2*a* to close. During a third period I of the waveform, there is again no mechanical stimulation of the plant 2. As can be seen during all three periods G, H, I there is very little identifiable activity which can be distinguished from background noise.

Figure 17B:
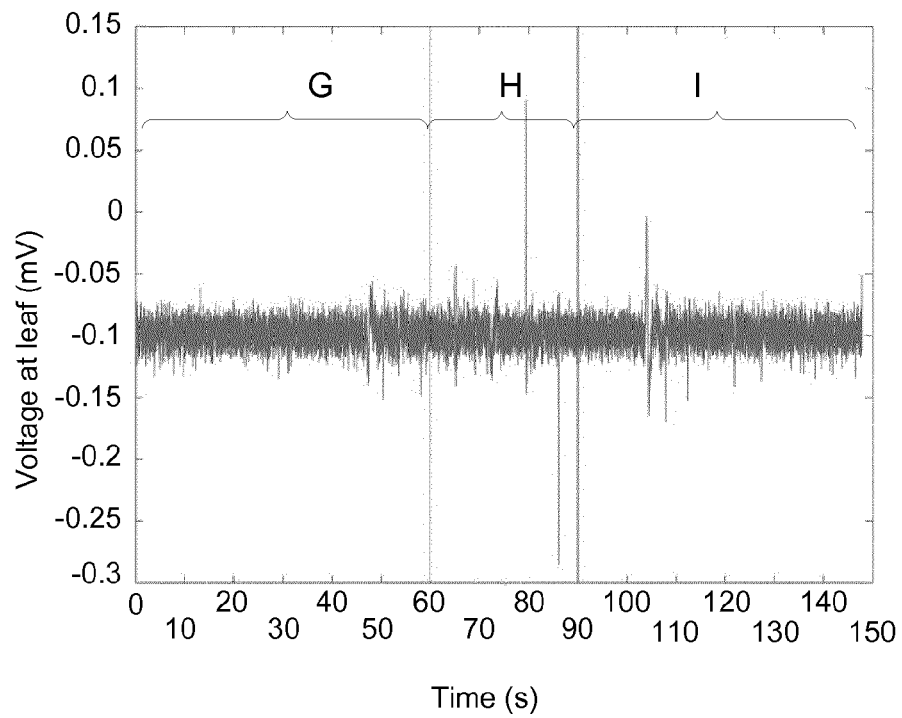

The captured electrical signal is processed by a moving average filter. The resulting processed signal is shown as FIG. 17*b*. As can clearly be seen during each of the three periods G, H, I, there are some transient electrical signals. A selection of these transient electrical signals are shown in more detail in FIGS. 10*a*, 10*b* and 10*c*.

Figure 18A:
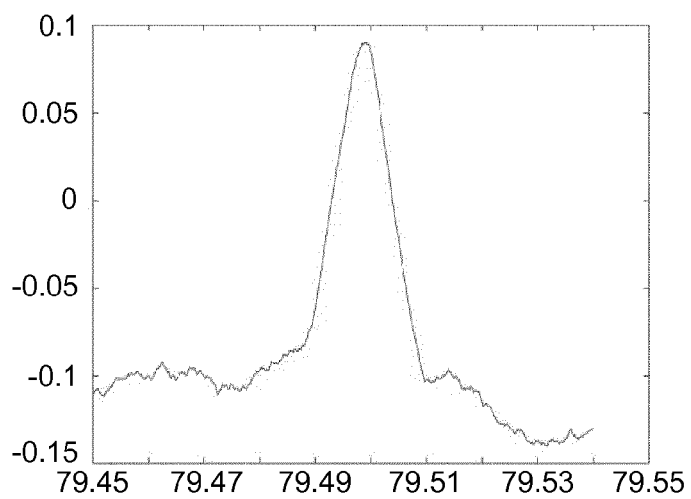
FIGS. 18a to 18c show portions of the signal shown in FIG. 9b.

FIG. 18*a* shows in more detail a transient electrical signal captured at time 79 s, and shows a clear peak of almost 0.2 mV in amplitude from the baseline potential value.

Figure 18B:
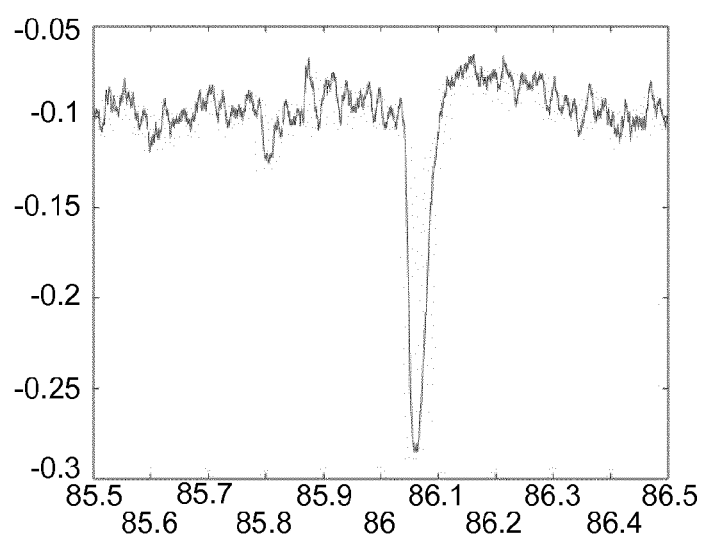

FIG. 18*b* shows in more detail a transient electrical signal captured at time 86 s, and shows a clear dip of almost 0.2 mV in amplitude from the baseline potential value.

Figure 18C:
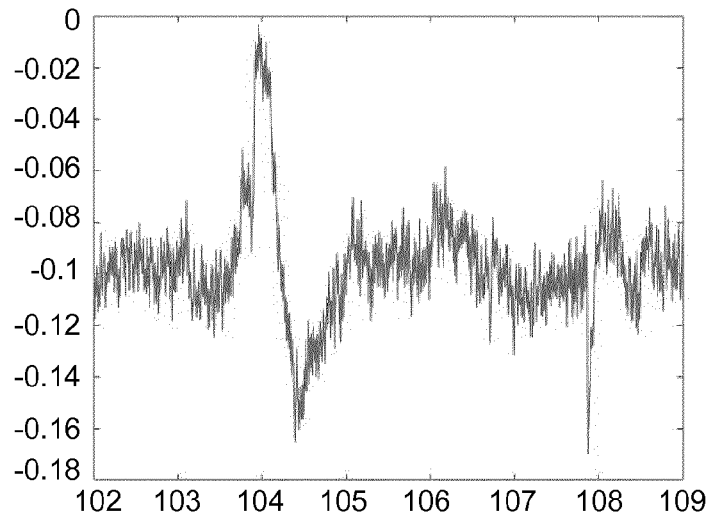

FIG. 18*c* shows in more detail a transient electrical signal captured at time 104 s, and shows a more complex feature which comprises an initial peak of around 0.1 mV, followed by a dip of around 0.05 mV in amplitude from the baseline potential value.

It is understood that the signals illustrated in FIGS. 18*a* to 18*c* provide evidence of communication as to the state of health or vitality of the plant to other parts of the plant.

As referred to above, transient electrical signals can be considered to be indicative of a state of a plant's health or vitality. Processing described above, for example with reference to FIG. 4, can be used to identify occurrences of particular transient electrical signals. Further, those transient electrical signals can also be used to influence the state of a plant.

This can be demonstrated by capturing an electrical signal from a plant, and re-playing the captured signal to the plant. When this technique is applied to a Venus flytrap, a recording of an action potential event during a mechanically stimulated closing can be re-played to an open leaf, causing it to close. However, while it may be considered that it is the action potential itself which is recorded and triggered, the recorded signal may also contain higher frequency, and lower amplitude components (such as, for example transient electrical signals as described above), which may be operative to cause the leaf to close.

The invention claimed is:

1. A method of processing signals comprising:
obtaining an electrical signal emitted by one or more plant specimens, the obtained electrical signal comprising at least one transient electrical signal component having a duration of the order of milliseconds to seconds;
processing said obtained electrical signal to generate plant data; and
generating a plant control signal based upon the plant data;
wherein the plant data is data indicative of a characteristic of said one or more plant specimens, wherein said characteristic comprises at least one of: a measure of the health of said one or more plant specimens, a measure of the vitality of said one or more plant specimens, and a reaction to environmental changes of said one or more plant specimens; wherein said processing comprises identifying one or more components of said obtained electrical signal which has a predetermined characteristic indicative of said characteristic of said one or more plant specimens.

2. A method according to claim 1, wherein the plant control signal is arranged to affect said one or more plant specimens.

3. A method according to claim 1, wherein the plant control signal is arranged to control at least one parameter of the environment of the one or more plant specimens.

4. A method according to claim 1, comprising controlling an environment of the one or more plant specimens based upon the plant data, wherein controlling an environment of the one or more plant specimens comprises controlling at least one of: the illumination of, the irrigation of, insecticide application to, fungicide application to, the temperature of, the humidity of, and the nutrition of said one or more plant specimens.

5. A method according to claim 1, wherein generating the plant control signal based upon the plant data comprises determining whether the plant data meets a predetermined criterion.

6. A method according to claim 5, wherein determining whether said plant data meets said predetermined criterion is based upon plant data relating to a plurality of plant specimens.

7. A method according to claim 1, wherein generating the plant control signal based upon the plant data comprises:
   determining whether the plant data meets a predetermined criterion; and
   generating the plant control signal if the plant data meets a predetermined criterion.

8. A method according to claim 1, wherein said processing comprises:
   comparing said obtained electrical signal with one or more reference signals; and
   identifying one or more components of said obtained electrical signal which has a predetermined relationship with said one or more reference signals.

9. A method according to claim 8, wherein comparing said obtained electrical signal with one or more reference signals comprises generating data indicative of a relationship between said obtained electrical signal and said one or more reference signals.

10. A method according to claim 9, wherein identifying one or more components of said obtained electrical signal which has a predetermined relationship with said one or more reference signals comprises determining whether said generated data satisfies a predetermined criterion.

11. A method according to claim 8, further comprising generating said one or more reference signals based upon a plurality of reference electrical signals obtained from one or more plant specimens while said one or more plant specimens are exposed to a predetermined condition.

12. A method according to claim 11, wherein said predetermined condition comprises at least one of: a thermal condition of said one or more plant specimens, a hydration condition of said one or more plant specimens, a nutrition condition of said one or more plant specimens, an illumination condition of said one or more plant specimens, a mechanical condition of said one or more plant specimens, an atmospheric condition of said one or more plant specimens, a threat associated with said one or more plant specimens, and a chemical condition of said one or more plant specimens.

13. A method according to claim 1, wherein obtaining the electrical signal comprises monitoring a potential difference between a reference electrode associated with a reference potential and a capture electrode in contact with said one or more plant specimens; wherein said reference electrode is in contact with a growth medium in contact with said one or more plant specimens.

14. A method according to claim 13, further comprising electromagnetically shielding an electrical signal obtained by said reference electrode and/or said capture electrode.

15. A method according to claim 1, wherein obtaining the electrical signal comprises electromagnetically shielding said one or more plant specimens during the obtaining of the electrical signal.

16. A method according to claim 1, wherein the obtained electrical signal comprising at least one signal component having a frequency of at least 10 Hz.

17. A method according to claim 1, further comprising communicating said plant data from a first processing device to second processing device, wherein:
   said first processing device is arranged to sense an electrical signal emitted by said one or more plant specimens; and
   said second processing device is a mobile computing device.

18. A method according to claim 1, wherein said processing comprises transforming said obtained electrical signal from a time domain signal to a frequency domain signal, said frequency domain signal comprising a plurality of frequency components each having a respective amplitude value.

19. A method according to claim 1, wherein said plant data comprises data indicative of at least one of: a thermal condition of said one or more plant specimens, a hydration condition of said one or more plant specimens, a nutrition condition of said one or more plant specimens, an illumination condition of said one or more plant specimens, a mechanical condition of said one or more plant specimens, an atmospheric condition of said one or more plant specimens, a threat associated with said one or more plant specimens, and a chemical condition of said one or more plant specimens.

20. Apparatus for processing signals, the apparatus comprising:
   a capture device configured to generate a signal based upon an electrical signal received from one or more plant specimens; said electrical signal being emitted by said one or more plant specimens, said electrical signal comprising at least one transient electrical signal component having a duration of the order of milliseconds to seconds;
   a processor arranged to:
      process said obtained electrical signal to generate plant data wherein the plant data is data indicative of a characteristic of said one or more plant specimens, said processing comprising identifying one or more components of said obtained electrical signal which has a predetermined characteristic indicative of said characteristic of said one or more plant specimens, wherein said characteristic comprises at least one of; a measure of the health of said one or more plant specimen, the vitality of said one or more plant specimen, or a reaction to environmental changes of said one or more plant specimens, and
      generate a plant control signal based upon the plant data.

21. Apparatus according to claim 20 further comprising at least one electrode configured to receive said electrical signal emitted by said one or more plant specimens.

22. Apparatus according to claim 20, further comprising shielding configured to reduce the effect of electromagnetic radiation upon said generated signal.

* * * * *